United States Patent
Ye et al.

(10) Patent No.: US 7,115,628 B2
(45) Date of Patent: Oct. 3, 2006

(54) BRIDGED PIPERIDINE DERIVATIVES AS MELANOCORTIN RECEPTOR AGONISTS

(75) Inventors: Zhixiong Ye, Princeton, NJ (US); Khaled J. Barakat, Brooklyn, NY (US); Liangqin Guo, Edison, NJ (US); Ravi P. Nargund, East Brunswick, NJ (US); Iyassu K. Sebhat, New York, NY (US)

(73) Assignee: Merck & Co., Inc., Rahway, NJ (US)

( * ) Notice: Subject to any disclaimer, the term of this patent is extended or adjusted under 35 U.S.C. 154(b) by 162 days.

(21) Appl. No.: 10/483,913

(22) PCT Filed: Jul. 12, 2002

(86) PCT No.: PCT/US02/22258

§ 371 (c)(1),
(2), (4) Date: Jan. 14, 2004

(87) PCT Pub. No.: WO03/007949

PCT Pub. Date: Jan. 30, 2003

(65) Prior Publication Data

US 2004/0180923 A1 Sep. 16, 2004

Related U.S. Application Data

(60) Provisional application No. 60/306,359, filed on Jul. 18, 2001.

(51) Int. Cl.
*A61K 31/44* (2006.01)
*C07D 471/08* (2006.01)

(52) U.S. Cl. .................. 514/304; 514/299; 546/112; 546/124

(58) Field of Classification Search .............. 514/299, 514/304; 546/112, 124
See application file for complete search history.

(56) References Cited

U.S. PATENT DOCUMENTS

| 5,281,585 A | 1/1994 | Duggan et al. |
| 5,576,290 A | 11/1996 | Hadley |
| 5,721,251 A * | 2/1998 | Chen et al. .................. 514/318 |
| 6,051,555 A | 4/2000 | Hadley |
| 6,166,037 A | 12/2000 | Budhu et al. |
| 6,350,760 B1 | 2/2002 | Bakshi et al. |
| 6,458,790 B1 * | 10/2002 | Palucki et al. ........... 514/237.2 |
| 2002/0091115 A1 | 7/2002 | Dyatkin et al. |

FOREIGN PATENT DOCUMENTS

| EP | 0 512 831 A1 | 11/1992 |
| EP | 0 512 831 B1 | 9/1999 |
| GB | 1115817 | 5/1968 |
| WO | WO 99/09984 | 3/1999 |
| WO | WO 99/64002 | 12/1999 |
| WO | WO 00/53148 | * 9/2000 |
| WO | WO 00/74649 | 12/2000 |
| WO | WO 00/74679 | 12/2000 |
| WO | WO 01/58891 | 8/2001 |
| WO | WO 01/70337 | 9/2001 |
| WO | WO 01/70708 | 9/2001 |
| WO | WO 01/91752 | 12/2001 |
| WO | WO 02/067869 | 9/2002 |
| WO | WO 02/068387 | 9/2002 |
| WO | WO 02/068388 | 9/2002 |
| WO | WO 03/009847 | 2/2003 |

OTHER PUBLICATIONS

Hall et al. "Obesity hypertension . . . " CA 136:67681 (2001).*
Mountjoy "Cloning of the melanocortin receptors" CA 134:703799 (2000).*
Villani et al. "Derivatives of 2-azabicyclo[2,2,2]octane . . . " J. Med. Chem. v.12, 933-4 (1969).*
Huszar et al., Cell, vol. 88 (1997), pp. 131-141, "Targeted disruption of the melanocortin-4 receptor results in obesity in mice".
Dinsmore et al., Brit. Med. J., vol. 318 (1999), pp. 387-390, "ABC of sexual health—erectile dysfunction".
Kask et al., Biochem. & Biophys. Res. Comm., vol. 245 (1998), pp. 90-93, "Selective antagonist for the melanocortin 4 receptor (HSO014) increases food intake in free-feeding rats".
Chen et al., Cell, vol. 91 (1997), pp. 789-798, "Exocrine gland dysfunction in MC5-R-deficient mice . . . ".
Gingell et al., Exp. Opin. Ther. Patents, vol. 9 (1999), pp. 1689-1696, "Emerging pharmacological therapies for erectile dysfunction".
Moreland et al., Life Sciences, vol. 62, No. 20 (1998), pp. PL-309-318, "Sildenafil, A novel inhibitor of phosphodiesterase Type 5 in human corpus cavernosum smooth muscle cells".
Giraudo et al., Brain Res. vol. 809 (1998), pp. 302-306, "Feeding effects of hypothalamic injection of melanocortin 4 receptor ligands".

(Continued)

*Primary Examiner*—Celia Chang
(74) *Attorney, Agent, or Firm*—Baerbel R. Brown; Melvin Winokur

(57) ABSTRACT

Certain novel bridged piperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

19 Claims, No Drawings

OTHER PUBLICATIONS

Graul, Drugs News & Perspectives, vol. 9 (1996), pp. 572-575, "Latest findings on the diagnosis and treatment of erectile dysfunction".

Street et al., J. Med. Chem., vol. 33 (1990), pp. 2690-2697, "Synthesis and biological activity of 1,2,4-oxadiazole derivatives . . . ".

Yang et al., Molec. Endocrinology, vol. 11 (1997), pp. 274-280, "Effects of recombinant agouti-signaling protein on melanocortin action".

McKenna et al., Pharmacol. Biochem. & Behavior, vol. 40 (1991), pp. 151-156, "Modulation by peripheral serotonin of the threshold for sexual reflexes in female rats".

Takahashi et al., Brain Res., vol. 359 (1985), pp. 194-207, "Dual estradiol action in diencephalon and the regulation of sociosexual behavior in female golden hamsters".

Olofson et al., J. Org. Chem., vol. 49 (1984), pp. 2081-2082, "A new reagent for the selective, high-yield N-dealkylation of tertiary amines . . . ".

Yoram et al., Current Opinion in Urology, vol. 7 (1997), pp. 349-353, "Oral pharmacotherapy in erectile dysfunction".

Heaton et al., Int'l J. of Importenc Res., vol. 9 (1997), pp. 115-121, "A therapeutic taxonomy of treatments for erectile dysfunction: an evolutionary imperative".

Dorr et al., Life Sciences, vol. 58, No. 20 (1996), pp. 1777-1784, "Evaluation of melanotan-II, a superpotent cyclic melanotropic peptide in a pilot phase-I clinical study".

Wessells et al., Urology, vol. 56 (2000), pp. 641-646, "Effect of an alpha-melanocyte stimulating hormone analog on penile erection and sexual desire in men with organic erectile dysfunction".

Campbell et al., Tetrahedron, vol. 48 (1992), pp. 8751-8774, "Synthesis of 5-homoshikimic acid and some fluorinated derivatives as potential inhibitors of 5-enolpyruvylshikimate-3-phosphate synthase".

McKenna et al., Am. J. Physiol. 261 (Regulatory Integrative Comp. Physiol. 30): R1276-R1285 (1991), "A model for the study of sexual function in anesthetized male and female rats".

Imai et al., Database STN No. 108:150205, Chem. Phar. Bull, vol. 35, No. 7 (1987), pp. 2646-2655, "Highly regioselective synthesis of trisubstituted pyrrolidines by 1,3-cycloaddition".

Getting et al., Chem. Abstracts., vol. 133:159566a (2000), "MC3-R as a novel target for antiinflammatory therapy".

Budhu et al., Chem. Abstracts., vol. 130:223167p (1999), "Preparation of piperidinylpyrrolidins as modulators of chemokine receptor activity".

Wessels et al., J. of Urology, vol. 160 (1998), pp. 389-393, "Synthetic melanotropic peptide initiates errections in men with psyhcogenic erectile dysfunction . . . ".

Uckert et al., Exp. Opin. Invest. Drugs, vol. 12 (2003), pp. 1521-1533, "Current and future trneds in the oral pharmacotherapy of male erectile dysfunction".

Chaki et al., Exp. Opinion on Therap. Patents, vol. 11 (2001), pp. 1677-1692, "Recent advances in feeding suppressing agents: potential therapeutic strategy for the treatment of obesity".

Corcos et al., Society for Neuroscience Abstracts, vol. 23 (1997), Abstract No. 267.9, p. 673, "HP 228 is a potent agonist of melanocortin receptor 4, and significantly attenuates obesity and diabetes in Zucker fatty rats".

Peptides: Frontiers of Peptide Science, Proceedings of the 15th American Peptide Symposium, Jun. 14-19, 1997, Nashville, TN.

Tomlinson et al., Database STN No. 135:166844 (2001), "Preparation of piperazinyl and piperidinyl ketones useful for treating or preventing neuronal damage and for stimulating nerve growth".

* cited by examiner

BRIDGED PIPERIDINE DERIVATIVES AS MELANOCORTIN RECEPTOR AGONISTS

CROSS-REFERENCE TO RELATED APPLICATIONS

This application is a U.S. National Phase application under 35 U.S.C. §371 of PCT Application No. PCT/US02/22258, filed Jul. 12, 2002, which claims priority under 35 U.S.C. §119 from U.S. Provisional Application No. 60/306,359, Jul. 18, 2001.

FIELD OF THE INVENTION

The present invention relates to bridged piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," *Brain Research*, 80: 302–306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., *Cell*, 88: 131–141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," *Biochem. Biophys. Res. Commun.*, 245: 90–93 (1998)). MC-5R is expressed in many tissues, including white fat, placenta and exocrine glands. A low level of expression is also observed in the brain. MC-5R knockout mice reveal reduced sebaceous gland lipid production (Chen et al., *Cell*, 91: 789–798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387–390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," *Exp. Opin. Ther. Patents* 9: 1689–1696 (1999)). Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," *Life Sci.*, 62: 309–318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. IC-351 (ICOS Corp.) is claimed to have greater selectivity for PDE-V over PDE-VI than sildenafil. Other PDE-V inhibitors include M-54033 and M-54018 from Mochida Pharmaceutical Co. and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives*, 9: 572–575 (1996); "Oral Pharmacotherapy in Erectile Dysfunction," *Current Opinion in Urology*, 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389–393 (1998); *Fifteenth American Peptide Symposium*, Jun. 14–19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology*, 56: 641–646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine and piperidine derivatives have been disclosed in WO 99/64002 (16 Dec. 1999) and WO 00/74679 (14 Dec. 2000), respectively, as agonists of the melanocortin receptor(s) and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

There is also a continuing need for improved pharmacological agents for the treatment of diabetes and obesity.

It is therefore an object of the present invention to provide bridged piperidine derivatives which are melanocortin receptor agonists and thereby useful to treat obesity, diabetes, male sexual dysfunction, and female sexual dysfunction.

It is another object of the present invention to provide bridged piperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin receptor in a subject in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a subject in need thereof.

It is another object of the present invention to provide methods for the treatment of erectile dysfunction by administering the compounds and pharmaceutical compositions of the present invention to a subject in need thereof.

These and other objects will become readily apparent from the detailed description that follows.

SUMMARY OF THE INVENTION

The present invention relates to novel bridged piperidine derivatives of structural formula I:

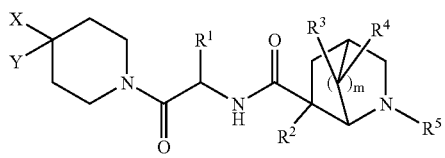

(I)

These bridged piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin receptor in a subject in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to treat the condition.

The present invention also relates to methods for treating or preventing diabetes by administering the compounds of the present invention in combination with a therapeutically effective amount of another agent known to be useful to treat the condition.

DETAILED DESCRIPTION OF THE INVENTION

The present invention relates to bridged piperidine derivatives useful as melanocortin receptor agonists. Representative compounds of the present invention are described by structural formula I:

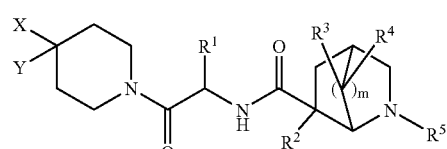

(I)

or a pharmaceutically acceptable salt thereof;
wherein m is 1 or 2;
each n is independently 0, 1, or 2;
each p is independently 0, 1 or 2;
q is 1 or 2;
$R^1$ is selected from the group consisting of
  hydrogen,
  $C_{1-8}$ alkyl,
  $(CHR^7)_n$—$C_{3-6}$ cycloalkyl,
  $(CHR^7)_q$—$O(CHR^7)$aryl,
  $(CHR^7)_n$-aryl, and
  $(CHR^7)_n$-heteroaryl;

wherein aryl and heteroaryl are unsubstituted or substituted with one to three groups independently selected from $R^6$; and alkyl and cycloalkyl are unsubstituted or substituted with one to three groups independently selected from $R^6$ and oxo;

$R^2$ is selected from the group consisting of
  hydrogen,
  $C_{1-8}$ alkyl,
  $(CH_2)_n C_{3-6}$ cycloalkyl, and
  $(CH_2)_n$-aryl;

$R^3$ and $R^4$ are each independently selected from the group consisting of
  hydrogen,
  $C_{1-8}$ alkyl,
  $(CH_2)_n C_{3-6}$ cycloalkyl,
  $(CH_2)_n$-aryl,
  hydroxy,
  halogen, and
  amino;

$R^5$ is selected from the group consisting of
  hydrogen,
  $C_{1-8}$ alkyl,
  $(CH_2)_n$-aryl,
  $(CH_2)_n C_{3-6}$ cycloalkyl,
  $(CH_2)_n$-heteroaryl,
  $(CH_2)_n$-heterocyclyl,
  $COC(R^7)_2 NH_2$,
  $COR^7$,
  $(CH_2)_n OR^7$,
  $(CH_2)_n CO_2 R^7$,
  $(CH_2)_n CONR^7 R^7$,
  $CH_2 C \equiv CH$,
  $CO_2 R^7$,
  $CH_2 CHF_2$,
  $CONR^7 R^7$, and
  $SO_2 R^7$;

wherein aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;

each $R^6$ is independently selected from the group consisting of
hydrogen,
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
$OR^7$,
$(CH_2)_nN(R^7)_2$,
$(CH_2)_nC\equiv N$,
$(CH_2)_nCO_2R^7$,
$NO_2$,
$(CH_2)_nNR^7SO_2R^7$,
$(CH_2)_nSO_2N(R^7)_2$,
$(CH_2)_nS(O)_pR^7$,
$(CH_2)_nNR^7C(O)N(R^7)_2$,
$(CH_2)_nC(O)N(R^7)_2$,
$(CH_2)_nNR^7C(O)R^7$,
$(CH_2)_nNR^7CO_2R^7$,
$O(CH_2)_nC(O)N(R^7)_2$,
$CF_3$,
$CH_2CF_3$,
$OCF_3$, and
$OCH_2CF_3$;

wherein phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and wherein any methylene ($CH_2$) carbon atom in $R^6$ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;

each $R^7$ is independently selected from the group consisting of
hydrogen,
$C_{1-8}$ alkyl,
$(CH_2)_n$-phenyl,
$(CH_2)_n$-naphthyl,
$(CH_2)_n$-heteroaryl, and
$(CH_2)_nC_{3-7}$ cycloalkyl;

wherein phenyl, naphthyl, and heteroaryl are unsubstituted or substituted with one to three groups independently selected from $R^6$; alkyl and cycloalkyl are unsubstituted or substituted with one to three groups independently selected from $R^6$ and oxo; and wherein any methylene ($CH_2$) carbon atom in $R^7$ is unsubstituted or substituted with one to two groups independently selected from halogen, hydroxy, and $C_{1-4}$ alkyl; or two $R^7$ groups together with the atom to which they are attached form a 5- to 8-membered mono- or bicyclic ring system optionally containing an additional heteroatom selected from O, S, and $NC_{1-4}$ alkyl;

each $R^8$ is independently selected from the group consisting of
hydrogen,
$(CH_2)_nC_{1-7}$ alkyl,
$(CH_2)_n$-aryl,
$(CH_2)_n$-heteroaryl,
$(CH_2)_n$-heterocyclyl, and
$(CH_2)_nC_{3-7}$ cycloalkyl;

wherein aryl and heteroaryl are unsubstituted or substituted with one to three groups independently selected from $R^6$; and alkyl, cycloalkyl, heterocyclyl, and $(CH_2)_n$ are unsubstituted or substituted with one to three groups independently selected from $R^6$ and oxo; or two substituents when on the same methylene ($CH_2$) carbon atom are taken together with the carbon atom to which they are attached to form a cyclopropyl group;

or two $R^8$ groups together with the atoms to which they are attached form a 5- to 8-membered mono- or bi-cyclic ring system optionally containing an additional heteroatom selected from O, S, $NR^7$, NBoc, and NCbz;

X is selected from the group consisting of
$C_{1-18}$ alkyl,
$(CH_2)_nC_{3-8}$ cycloalkyl,
$(CH_2)_n$-phenyl,
$(CH_2)_n$-naphthyl,
$(CH_2)_n$-heteroaryl,
$(CH_2)_n$heterocyclyl,
$(CH_2)_nC\equiv N$,
$(CH_2)_nCON(R^8R^8)$,
$(CH_2)_nCO_2R^8$,
$(CH_2)_nCOR^8$,
$(CH_2)_nNR^8C(O)R^8$,
$(CH_2)_nNR^8CO_2R^8$,
$(CH_2)_nNR^8C(O)N(R^8)_2$,
$(CH_2)_nNR^8SO_2R^8$,
$(CH_2)_nS(O)_pR^8$,
$(CH_2)_nSO_2N(R^8)(R^8)$,
$(CH_2)_nOR^8$,
$(CH_2)_nOC(O)R^8$,
$(CH_2)_nOC(O)OR^8$,
$(CH_2)_nOC(O)N(R^8)_2$,
$(CH_2)_nN(R^8)(R^8)$, and
$(CH_2)_nNR^8SO_2N(R^8)(R^8)$;

wherein phenyl, naphthyl, and heteroaryl are unsubstituted or substituted with one to three groups independently selected from $R^6$; alkyl, cycloalkyl, and heterocyclyl are unsubstituted or substituted with one to three groups independently selected from $R^6$ and oxo; and wherein any methylene ($CH_2$) carbon atom in X is unsubstituted or substituted with one to two groups independently selected from halogen, hydroxy, and $C_{1-4}$ alkyl; and Y is selected from the group consisting of
hydrogen,
$C_{1-8}$ alkyl,
$C_{2-6}$ alkenyl,
$(CH_2)_nC_{3-8}$ cycloalkyl,
$(CH_2)_n$-phenyl,
$(CH_2)_n$-naphthyl,
$(CH_2)_n$-heteroaryl, and
$(CH_2)_n$-heterocyclyl;

wherein phenyl, naphthyl, and heteroaryl are unsubstituted or substituted with one to three groups independently selected from $R^6$; alkyl, cycloalkyl, and heterocyclyl are optionally substituted with one to three groups independently selected from $R^6$ and oxo; and wherein any methylene ($CH_2$) carbon atom in Y is unsubstituted or substituted with one to two groups independently selected from halogen, hydroxy, and $C_{1-4}$ alkyl.

In one embodiment of the compounds of formula I, $R^1$ is $CHR^7$-aryl, $CHR^7OCHR^7$-aryl, or $CHR^7$-heteroaryl wherein aryl and heteroaryl are unsubstituted or substituted with one to two groups independently selected from $R^6$. In a class of this embodiment, $R^1$ is benzyl optionally substituted with one or two groups independently selected from halogen, $C_{1-4}$ alkyl, $C_{1-4}$ alkoxy, CN, $CF_3$, and $OCF_3$. In a subclass of this class, $R^1$ is 4-chlorobenzyl; 4-fluorobenzyl; 3,4-difluorobenzyl; 3,5-difluorobenzyl; 2-cyano-4-fluorobenzyl; or 4-methoxybenzyl.

In a second embodiment of compounds of formula I, $R^2$ is hydrogen or $CH_3$.

In a third embodiment of compounds of formula I, $R^5$ is selected from the group consisting of
hydrogen,
$C_{1-8}$ alkyl,
$(CH_2)_n$-aryl,
$(CH_2)_n$-heteroaryl,
$(CH_2)_n$-heterocyclyl,
$(CH_2)_nC_{3-6}$ cycloalkyl,
$(CH_2)_nCO_2R^7$,
$(CH_2)_nCONR^7R^7$,
$(CH_2)_nOR^7$,
$COC(R^7)NH_2$,
$CH_2C\equiv CH$, and
$CH_2CHF_2$;
wherein aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo.

In a fourth embodiment of compounds of formula I, X is $C_{1-6}$ alkyl, $(CH_2)_n$-aryl, $(CH_2)_n$-heteroaryl, $(CH_2)_n$-heterocyclyl, $(CH_2)_nC(O)N(R^8)(R^8)$, $(CH_2)_nCO_2R^8$, $(CH_2)_nOR^8$, $(CH_2)_nS(O)_{0-2}R^8$, $(CH_2)_nNHC(O)R^8$, $(CH_2)_nOC(O)NR^8R^8$, or $(CH_2)_nNR^8SO_2R^8$; wherein aryl and heteroaryl are optionally substituted with one to three groups independently selected from $R^6$; heterocyclyl is optionally substituted with one to three groups independently selected from $R^6$ and oxo; the $(CH_2)_n$ group is optionally substituted with one to three groups independently selected from $R^7$, halogen, $S(O)_{0-2}R^7$, $N(R^7)_2$, and $OR^7$; and each $R^8$ is independently selected from H, $C_{1-8}$ alkyl, and $C_{3-6}$ cycloalkyl, wherein alkyl and cycloalkyl are optionally substituted with one to three groups independently selected from $R^6$ and oxo; or two $R^8$ groups together with the atoms to which they are attached form a 5- to 8-membered mono- or bi-cyclic ring system optionally containing an additional heteroatom selected from O, S, $NR^7$, NBoc, and NCbz.

In a class of this fourth embodiment, X is $C_{1-6}$ alkyl, $(CH_2)_{0-1}$-heteroaryl, $CH_2$-heterocyclyl, $CO_2R^8$, $CH_2OR^8$, $CH_2S(O)_{0-2}R^8$, $NHC(O)R^8$, $CH_2NR^8SO_2R^8$, $CH_2OC(O)NR^8R^8$, $CH_2NR^8SO_2R^8$, or $C(O)N(R^8)(R^8)$; wherein heteroaryl is optionally substituted with one to three groups independently selected from $R^6$; heterocyclyl is optionally substituted with one to three groups independently selected from $R^6$ and oxo; and each $R^8$ is independently selected from H, $C_{1-8}$ alkyl, and $C_{3-6}$ cycloalkyl, wherein alkyl and cycloalkyl are optionally substituted with one to three groups independently selected from $R^6$ and oxo; or two $R^8$ groups together with the atoms to which they are attached form a 5- to 8-membered mono- or bi-cyclic ring system optionally containing an additional heteroatom selected from O, S, $NR^7$, NBoc, and NCbz.

In a fifth embodiment of compounds of formula I, Y is $C_{1-8}$ alkyl, $(CH_2)_nC_{3-7}$ cycloalkyl, $(CH_2)_n$-aryl, $(CH_2)_n$-heterocyclyl, or $(CH_2)_n$-heteroaryl; wherein aryl and heteroaryl are optionally substituted with one to three groups independently selected from $R^6$; and $(CH_2)_n$, alkyl, cycloalkyl, and heterocyclyl are optionally substituted with one to three groups independently selected from $R^6$ and oxo. In a class of this embodiment, Y is cyclohexyl, cycloheptyl, cyclopentyl, or $C_{1-6}$ alkyl, wherein alkyl and cycloalkyl are unsubstituted or substituted with one to three groups independently selected from $R^6$ and oxo. In a subclass of this class, Y is cyclohexyl or $C_{1-6}$ alkyl, wherein the cyclohexyl and alkyl groups are unsubstituted or substituted with one to three groups independently selected from $R^6$ and oxo.

In yet a further embodiment of the present invention, there are provided compounds of structural formula II:

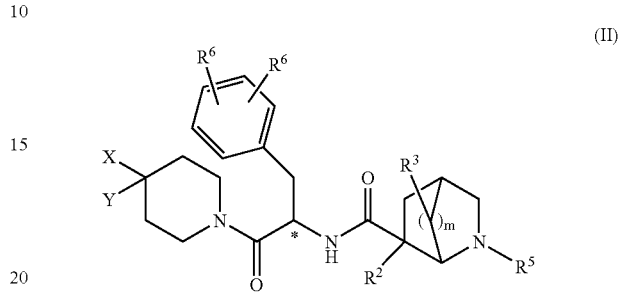

(II)

wherein m is 1 or 2;
each n is independently 0, 1, or 2;
$R^2$ is hydrogen or methyl;
$R^3$ is hydrogen, fluoro, or hydroxy;
each $R^6$ is independently selected from the group consisting of
hydrogen,
halogen,
cyano,
$C_{1-4}$ alkyl,
$C_{1-4}$ alkoxy,
trifluoromethyl, and
trifluoromethoxy;
$R^5$ is selected from the group consisting of
hydrogen,
$C_{1-8}$ alkyl,
$(CH_2)_n$-aryl,
$(CH_2)_n$-heteroaryl,
$(CH_2)_n$-heterocyclyl,
$(CH_2)_nC_{3-6}$ cycloalkyl,
$(CH_2)_nCO_2R^7$,
$(CH_2)_nCONR^7R^7$,
$(CH_2)_nOR^7$,
$COC(R^7)NH_2$,
$CH_2C\equiv CH$, and
$CH_2CHF_2$;
wherein aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;
Y is selected from the group consisting of
$C_{5-7}$ cycloalkyl and
$C_{1-6}$ alkyl;
wherein alkyl and cycloalkyl are unsubstituted or substituted with one to three groups independently selected from $R^6$ and oxo; and
X is selected from the group consisting of

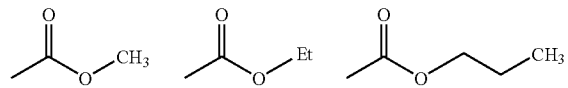

-continued
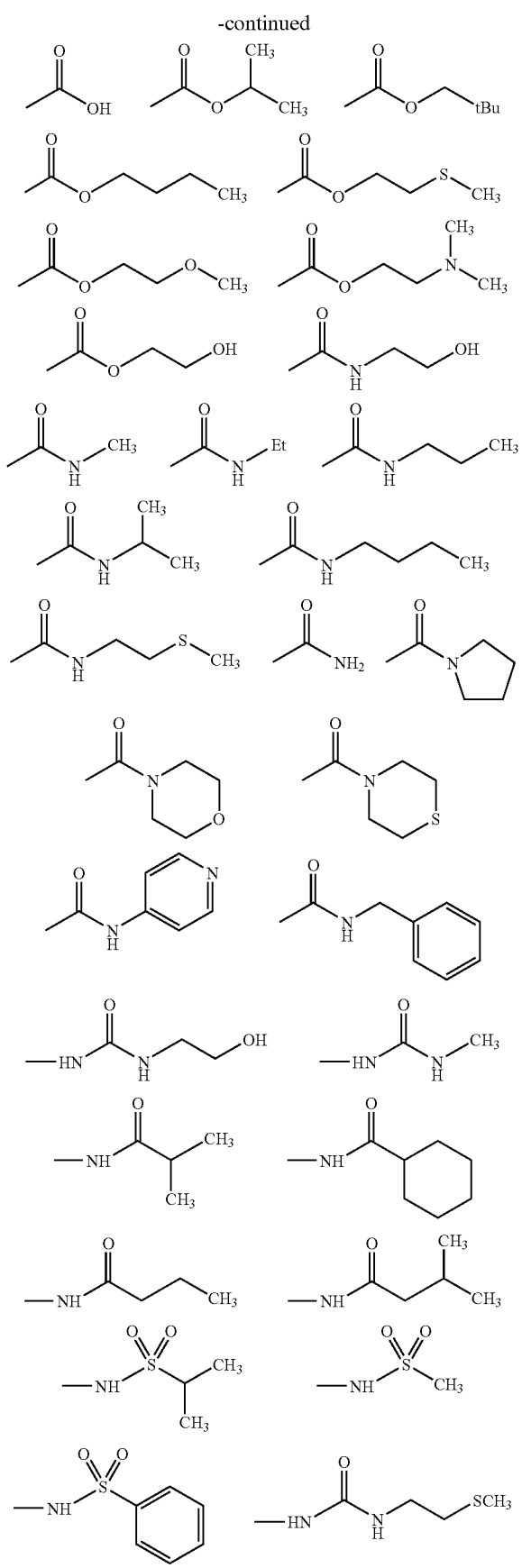 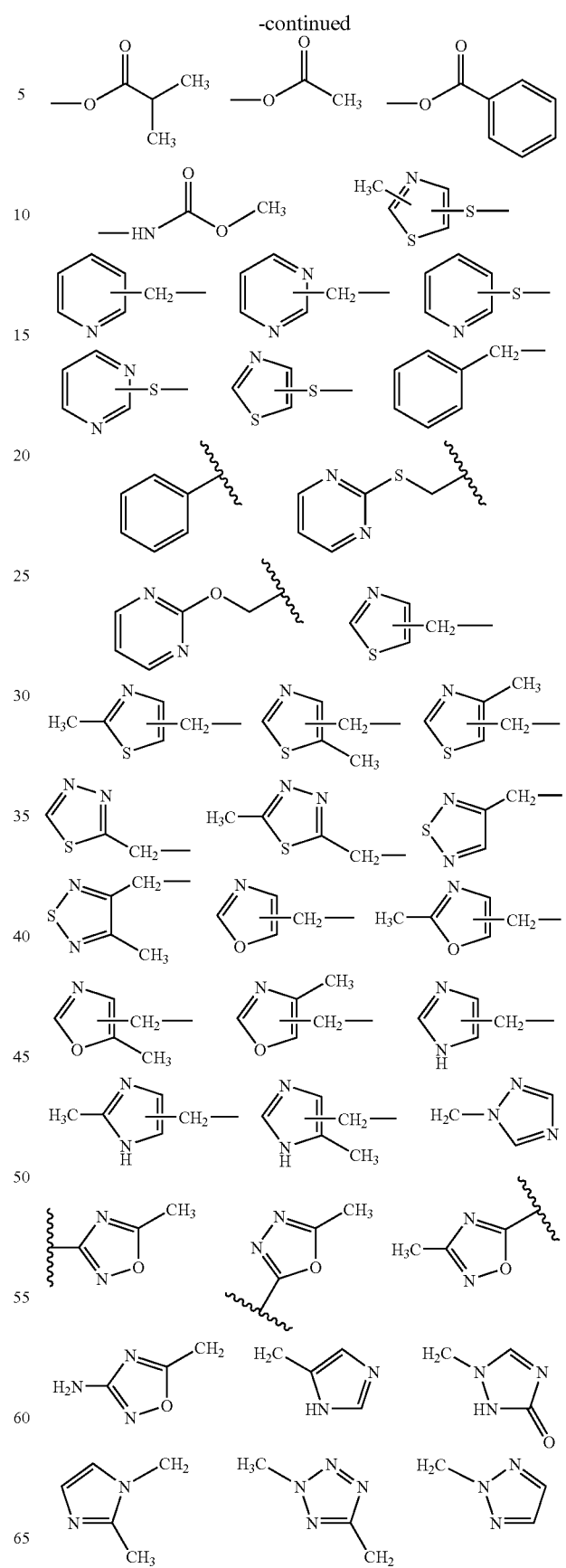

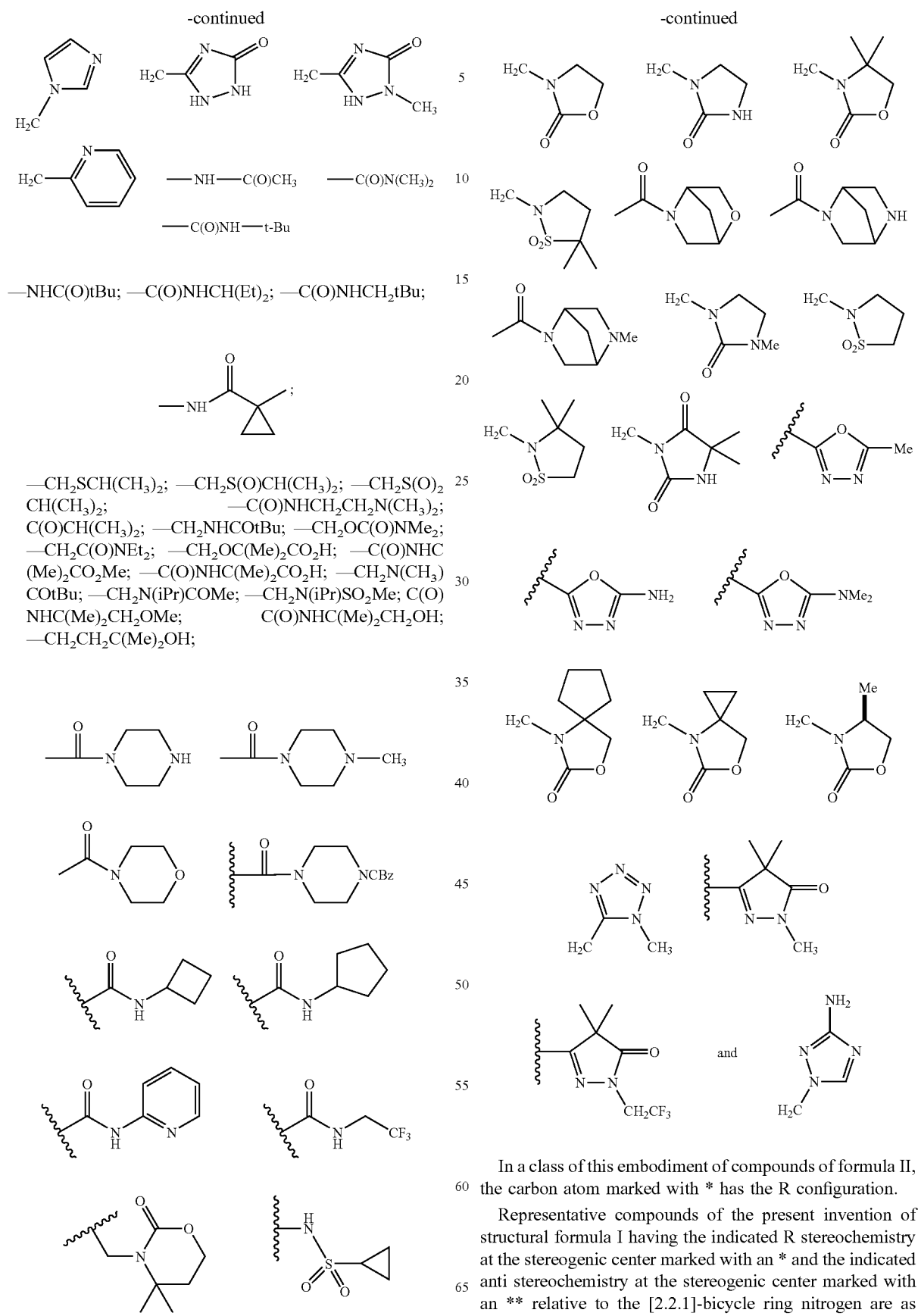

In a class of this embodiment of compounds of formula II, the carbon atom marked with * has the R configuration.

Representative compounds of the present invention of structural formula I having the indicated R stereochemistry at the stereogenic center marked with an * and the indicated anti stereochemistry at the stereogenic center marked with an ** relative to the [2.2.1]-bicycle ring nitrogen are as follows:

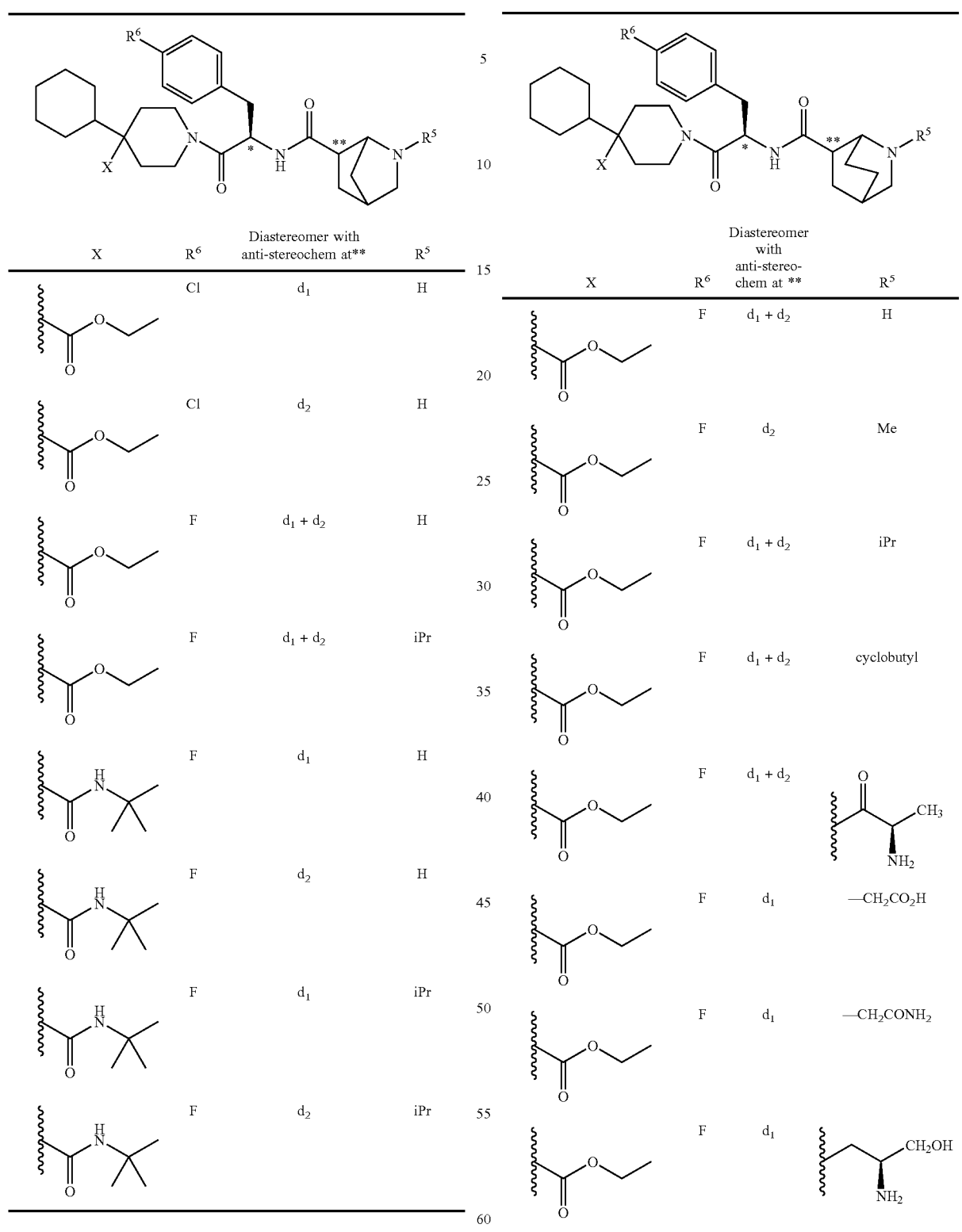

-continued

| X | R⁶ | Diastereomer with anti-stereo-chem at ** | R⁵ |
|---|---|---|---|
| ethyl ester (–C(O)OEt) | F | d₁ | —COCH₂NH₂ |
| –C(O)NH-tBu | F | d₁ + d₂ | H |
| –C(O)NH-tBu | Cl | d₁ + d₂ | Me |
| –C(O)NH-tBu | Cl | d₁ + d₂ | iPr |
| –C(O)NH-tBu | F | d₁ + d₂ | cyclobutyl |
| –C(O)NH-tBu | F | d₁ | 2,2-difluoroethyl |
| –C(O)NH-tBu | F | d₁ | –C(O)CH(NH₂)CH₃ |
| –C(O)NH-tBu | Cl | d₁ + d₂ | H |
| –C(O)NHMe | Cl | d₁ + d₂ | H |

-continued

| X | R⁶ | Diastereomer with anti-stereo-chem at ** | R⁵ |
|---|---|---|---|
| –C(O)OCH₂CH₂OMe | F | d₁ + d₂ | H |
| –CH₂-(1,2,4-triazol-1-yl) | Cl | d₁ + d₂ | H |
| –CH₂-(1,2,4-triazol-1-yl) | F | d₁ + d₂ | iPr |
| –CH₂-(4,4-dimethyl-2-oxo-oxazolidin-3-yl) | F | d₁ + d₂ | H |
| –CH₂-(4,4-dimethyl-2-oxo-oxazolidin-3-yl) | F | d₁ | Me |
| –CH₂C(O)NEt₂ | F | d₁ + d₂ | H |
| –CH₂C(O)NEt₂ | F | d₁ + d₂ | cyclobutyl |
| –NHC(O)tBu | F | d₁ + d₂ | Me |
| –NHC(O)(1-methylcyclopropyl) | F | d₁ + d₂ | Me |

Yet further illustrative are the compounds selected from the group consisting of:
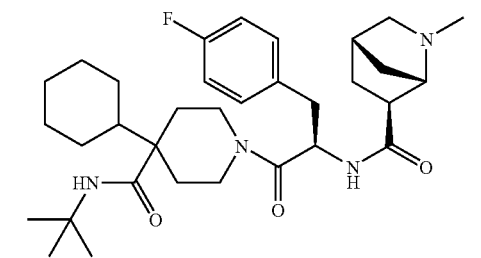
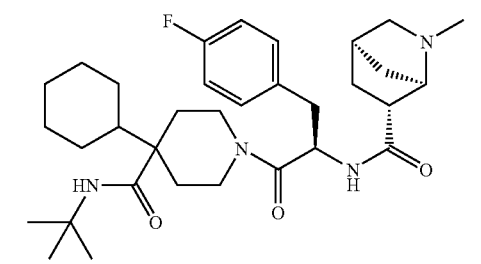
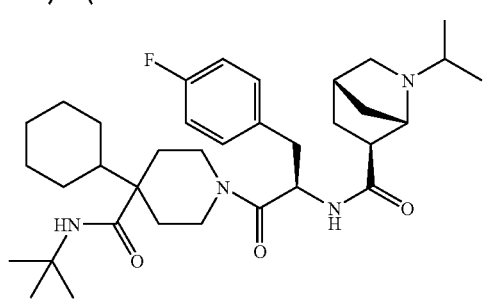
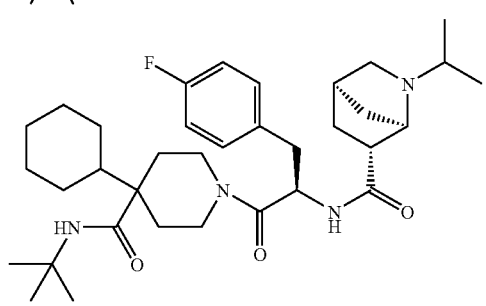
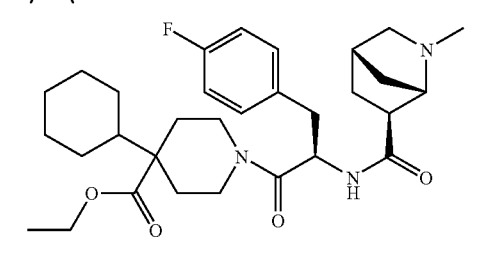
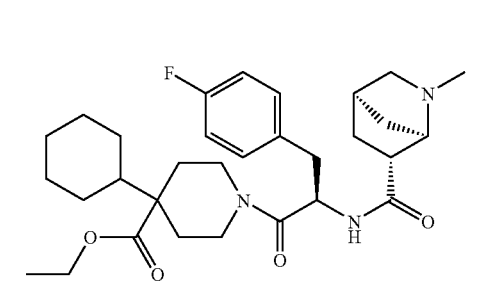
-continued
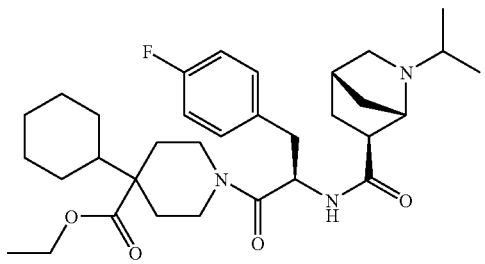
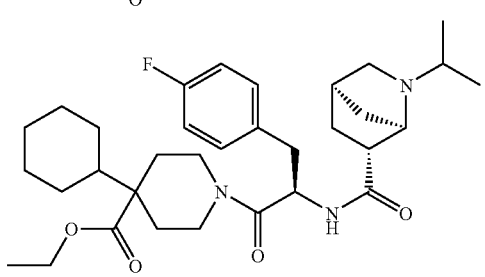
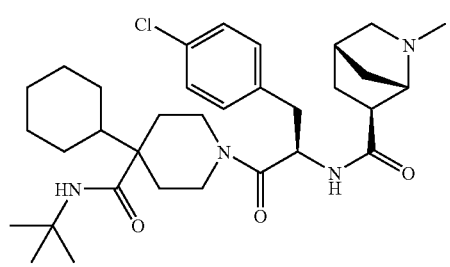
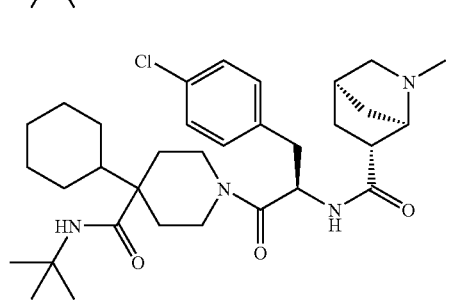
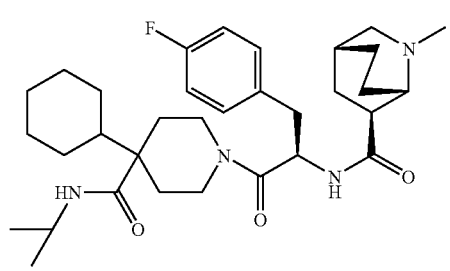
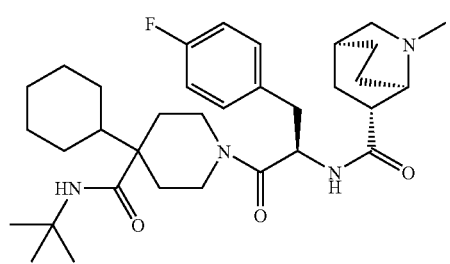

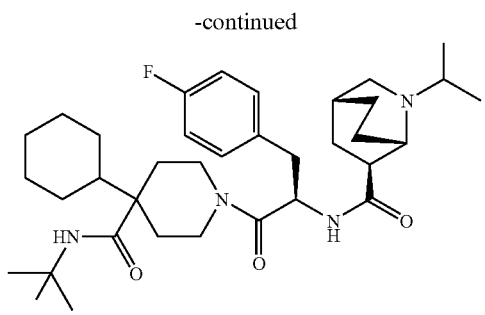

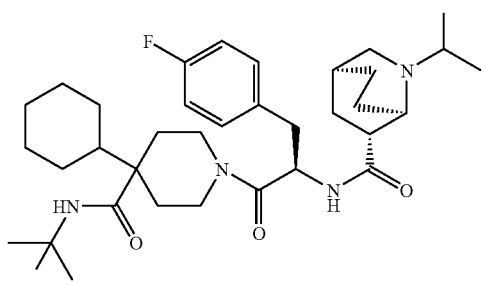

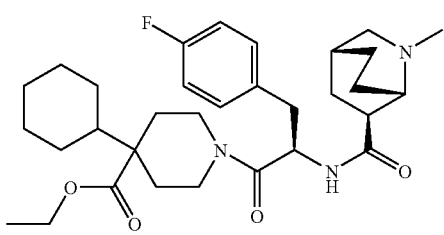

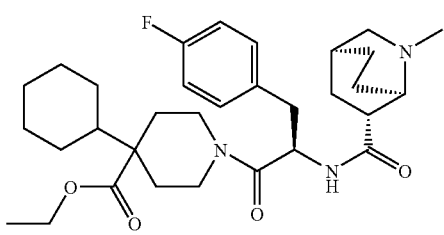

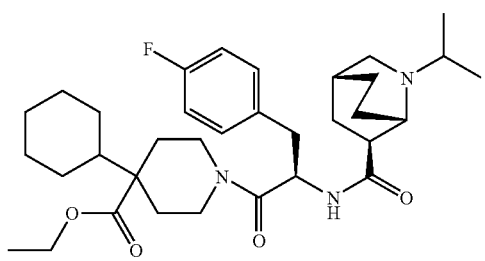

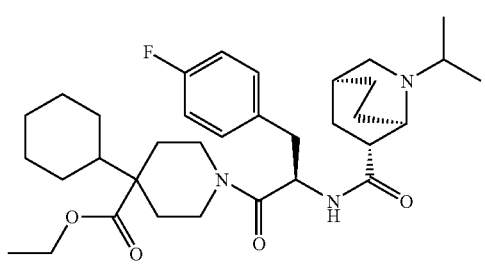

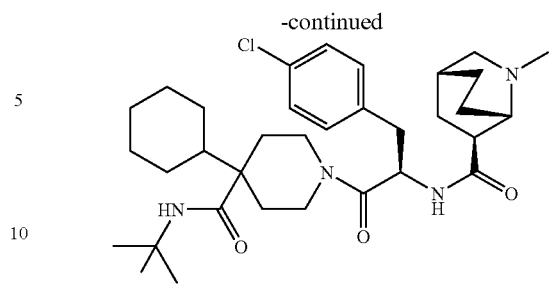

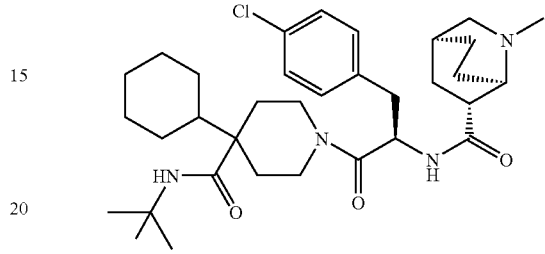

or a pharmaceutically acceptable salt thereof.

The compounds of structural formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a subject in need thereof which comprises administering to said subject a therapeutically or prophylactically effective amount of a compound of structural formula I.

Another aspect of the present invention provides a method for the treatment or prevention of male or female sexual dysfunction including erectile dysfunction which comprises administering to a subject in need of such treatment or prevention a therapeutically or prophylactically effective amount of a compound of structural formula I.

Another aspect of the present invention provides a pharmaceutical composition comprising a compound of structural formula I and a pharmaceutically acceptable carrier.

Yet another aspect of the present invention provides a method for the treatment or prevention of male or female sexual dysfunction including erectile dysfunction which comprises administering to a subject in need of such treatment or prevention a therapeutically or prophylactically effective amount of a compound of structural formula I in combination with a therapeutically effective amount of another agent known to be useful for the treatment of these conditions.

Yet another aspect of the present invention provides a method for the treatment or prevention of obesity which comprises administering to a subject in need of such treatment or prevention a therapeutically or prophylactically effective amount of a compound of structural formula I in combination with a therapeutically effective amount of another agent known to be useful for the treatment of this condition.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "$C_{1-4}$ alkyliminoyl" means C13C(=NH)—.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-Membered heteroaryl" represents a monocyclic heteroaromatic ring; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^7R^7$ may represent $NH_2$, $NHCH_3$, $N(CH_3)CH_2CH_3$, and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent.

The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I. Thus, the present invention is meant to encompass the stereoisomers depicted in the following structural formulae:

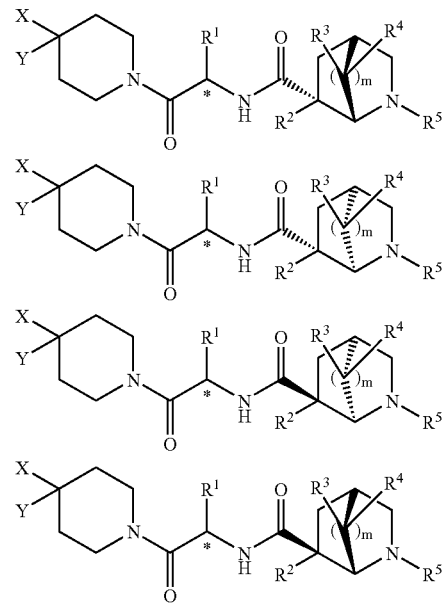

wherein the stereochemistry at the stereogenic center marked with an * can be either R or S.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I and II may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor relative to MC-1R, MC-2R, MC-3R, and MC-5R, which makes them especially useful in the prevention and treatment of obesity, as well as male and/or female sexual dysfunction, including erectile dysfunction.

"Male sexual dysfunction" includes impotence, loss of libido, and erectile dysfunction.

"Erectile dysfunction" is a disorder involving the failure of a male mammal to achieve erection, ejaculation; or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response:

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose), (e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) anti-obesity serotonergic agents, such as fenfluramine, dexfenfluramine, phentermine, and sibutramine;

(h) β3-adrenoreceptor agonists;

(i) pancreatic lipase inhibitors, such as orlistat;

(j) feeding behavior modifying agents, such as neuropeptideY Y1 and Y5 antagonists, such as those disclosed in WO 97/19682, WO 97/20820, WO 97/20821, WO 97/20822, WO 97/20823, WO 01/14376, and U.S. Pat. No. 6,191,160;

(k) orexin-1 receptor antagonists;

(l) PPARα agonists such as described in WO 97/36579 by Glaxo;

(m) PPARγ antagonists as described in WO97/10813;

(n) serotonin reuptake inhibitors such as fluoxetine, paroxetine, and sertraline;

(o) growth hormone secretagogues, such as MK-0677;

(p) cannabinoid receptor ligands, such as cannabinoid $CB_1$ receptor antagonists or inverse agonists, and (q) protein tyrosine phosphatase-1B (PTP-1B) inhibitors.

Examples of anti-obesity agents that can be employed in combination with a compound of Formula I are disclosed in "Patent focus on new anti-obesity agents," *Exp. Opin. Ther. Patents*, 10: 819–831 (2000) and in "Novel anti-obesity drugs," *Exp. Opin. Invest. Drugs*, 9: 1317–1326 (2000). The role of neuropeptide Y in obesity is discussed in *Exp. Opin. Invest. Drugs*, 9: 1327–1346 (2000). Cannabinoid receptor ligands are discussed in *Exp. Opin. Invest. Drugs*, 9: 1553–1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R,12aR)-2,3,6,7,12,12a-hexahydro-2-methyl-6-(3,4-methylenedioxyphenyl)pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in PCT International Application Publications WO 99/64002 (16 Dec. 1999) and WO 00/74679 (14 Dec. 2000), which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations used in the Description of the Preparation of the Compounds of the Present Invention:

| | |
|---|---|
| BOC (boc) | t-butyloxycarbonyl |
| BOP | benzotriazol-1-yloxytris(dimethylamino)phosphonium hexafluorophosphate |
| Bu | butyl |
| calc. | calculated |
| CBZ (Cbz) | benzyloxycarbonyl |
| c-hex | cyclohexyl |
| c-pen | cyclopentyl |

| | -continued |
|---|---|
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| EDC | 1-(3-dimethylaminopropyl)3-ethylcarbodiimide HCl |
| eq. | equivalent(s) |
| ES-MS | electron spray ion-mass spectroscopy |
| Et | ethyl |
| EtOAc | ethyl acetate |
| HATU | O-(7-azabenzotriazol-1-yl)-1,1,3,3-tetramethyluronium hexafluorophosphate |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-$x$R | melanocortin receptor ($x$ being a number) |
| Me | methyl |
| MF | molecular formula |
| MS | mass spectrum |
| Ms | methanesulfonyl |
| OTf | trifluoromethanesulfonyl |
| Ph | phenyl |
| Phe | phenylalanine |
| Pr | propyl |
| prep. | prepared |
| PyBrop | bromo-tris-pyrrolidino-phosphonium hexafluorophosphate |
| r.t. | room temperature |
| TFA | trifluoroacetic acid |
| THF | tetrahydrofuran |
| TLC | thin-layer chromatography. |

Reaction Schemes A and B illustrate the methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a 4-substituted piperidine of general formula 1 with an amino acid derivative of general formula 2 followed by removal of the amine protecting group Q affords an intermediate amine of general formula 3. The amine of formula 3 is then coupled with an N-protected bridged piperidine carboxylic acid of general formula 4 to afford a protected dipeptide of general formula 5. The two amide bond coupling reactions illustrated in reaction Scheme A are conducted in an appropriate inert solvent such as dimethylformamide (DMF), methylene chloride or the like and may be performed with a variety of reagents suitable for amide coupling reactions such as O-(7-azabenzotriazol-1-yl)-1,1, 3,3-tetramethyluronium hexafluorophospbate (HATU), 1-(3-dimethylaminopropyl)-3-ethylcarbodiimide hydrochloride (EDC) or benzotriazol-1-yloxytripyrrolidinephosphonium hexafluorophosphate (PyBOP). Preferred conditions for the amide bond coupling reactions shown in reaction Scheme A are known to those skilled in organic synthesis. Such modifications may include, but are not limited to, the use of basic reagents such as triethylamine (TEA) or N-methylmorpholine (NMM), or the addition of an additive such as 1-hydroxy-7-azabenzotriazole (HOAt) or 1-hydroxybenzotriazole (HOBt). Alternatively, 4-substituted piperidines of formula 1 may be treated with an active ester or acid chloride derived from carboxylic acid 2 or 4 which also affords compounds of structural formula I. The amide bond couplings shown in reaction Scheme A are usually conducted at temperatures between 0° C. and room temperature, occasionally at elevated temperatures, and the coupling reactions are typically conducted for periods of 1 to 24 hours.

If it is desired to produce a compound of structural formula I wherein $R^5$ is a hydrogen, the N-BOC or N-Cbz protected, analogs of structural formula I may be used in the synthesis and either Boc-deprotected under acidic conditions, for instance using trifluoroacetic acid in a solvent like methylene chloride or hydrogen chloride in a solvent such as ethyl acetate at room temperature, or Cbz-deprotected by catalytic hydrogenation.

When it is desired to prepare compounds of structural formula I wherein $R^5$ is not a hydrogen, the compounds of general formula I ($R^5$=H) may be further modified using the methodology described below in reaction Scheme B.

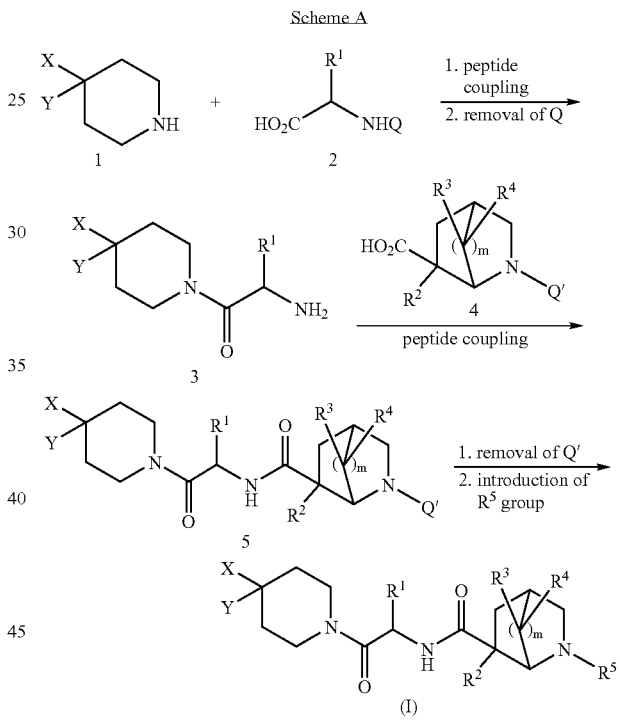

Scheme A

Reaction Scheme B illustrates general methods for the elaboration of an $R^5$ substituent following assembly of a compound of structural formula I (wherein $R^5$=BOC or Cbz) as described in reaction Scheme A. Either the N-BOC protected compound of structural formula I is first deprotected under acidic conditions for instance by treatment with hydrogen chloride in ethyl acetate or using trifluoroacetic acid in dichloromethane, or the N-Cbz protected compound is deprotected by catalytic hydrogenation. The resulting heterocyclic compound of structural formula I ($R^5$=H) may then be subjected to one of several alkylation strategies known in organic chemistry. For instance, compounds (I) ($R^5$=H) may be utilized in a reductive amination reaction with a suitable carbonyl containing partner (6). The reductive amination is achieved by initial formation of an imine between the amine of formula I ($R^5$=H) and either an aldehyde or ketone of formula 6. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (I) ($R^5$=H) may be directly alkylated using an alkylating agent such as 7 in a polar aprotic solvent such as DMF. In this reaction, the substituent Z of compound 7 is a good leaving group such as a halide, mesylate or triflate and the product is the compound of structural formula I bearing the $R^5$ substituent.

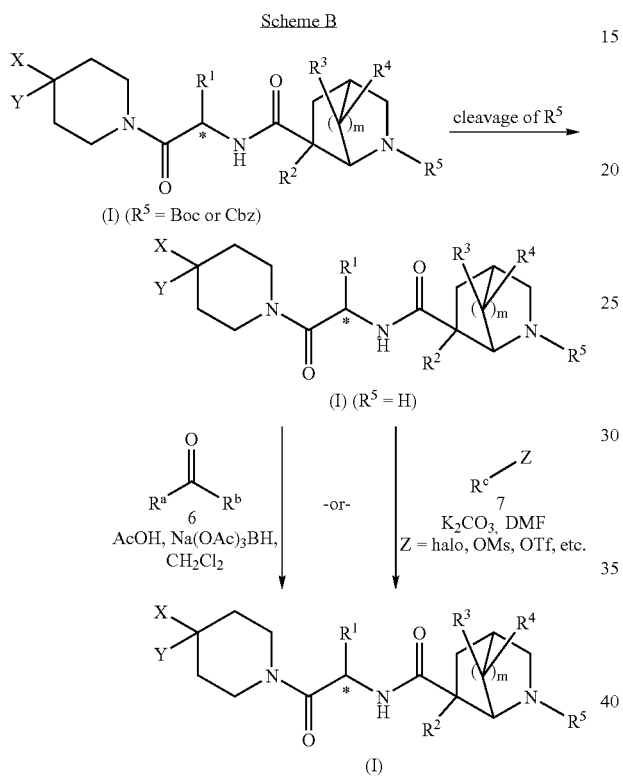

Preparation of N-Protected Bridged Piperidines of General Formula 4:

The N-protected bridged piperidine intermediates of general formula 4 for coupling with a peptide of general formula 3 as in Scheme A can be obtained from commercial sources or can be prepared following procedures described in the published chemical literature or modifications thereof that are in the purview of one of ordinary skill in the art of synthetic organic chemistry.

Preparation of 4-Substituted Piperidine Intermediates General Formula 1:

The preparation of 4-substituted piperidine intermediates of general structure 1 in Scheme A for coupling with the appropriate carboxylic acid intermediates of general structure 2 in Scheme A is disclosed in PCT International Application WO 00/74679 (14 Dec. 2000), which is incorporated by reference herein in its entirety. The synthesis of additional 4-substituted piperidine intermediates needed to prepare the compounds of the present invention is provided below.

Piperidine Intermediate 1:

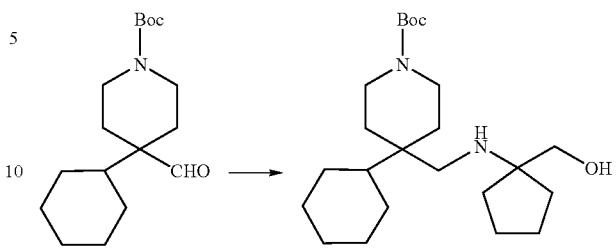

To a solution of 4-cyclohexyl 4-formyl-N-(tertbutyloxycarbonyl)piperidine (2.56 g, 8.68 mmol) in toluene (100 ml) was added acetic acid (2 ml) and 1-amino-1-cyclopentanemethanol (1.0 g, 8.68 mmol). After refluxing by using a Dean-Stark apparatus for 11 hours, the reaction mixture was concentrated. The residue was dissolved in acetic acid (70 ml) and hydrogenated overnight in the presence of platinum oxide (500 mg) under a balloon atmosphere of hydrogen gas. The catalyst was filtered off and solvent was removed to give a colorless oil, which was dissolved in methanol and made basic by addition of NaOH(5N, 4 ml) and concentrated. The residue was partitioned between water and $CH_2Cl_2$, the two layers separated, and the aqueous layer extracted with $CH_2Cl_2$. The combined organic extracts were washed with brine, dried over $MgSO_4$ and concentrated to give the title compound as a colorless oil (2.1 g).

MS: calc.for $C_{23}H_{42}N_2O_3$: 394.3; Found: 395 (M+1), 417 (M+Na).

Piperidine Intermediate 2:

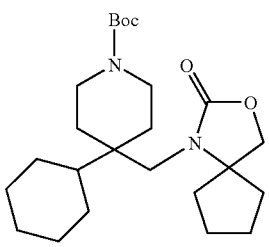

To a solution of Intermediate 1 (2.1 g, 5.33 mmol) in $CH_2Cl_2$ (70 ml) at 0° was added DMAP (0.65 g, 5.33 mmol), DIEA (3.76 ml, 21.3 mmol) followed by slow addition of phosgene (4.1 ml, 8.0 mmol). After stirring the reaction mixture for one hour at 0° C., the ice-water bath was removed and the reaction mixture was continued to stir at room temperature overnight. The mixture was diluted with $CH_2Cl_2$, washed with water and brine, dried over $MgSO_4$ and concentrated to give crude product, which was purified by column chromatography on silica gel (2% EtOAc/$CH_2Cl_2$ to 5% EtOAc/$CH_2Cl_2$) to give the title compound as a white solid (1.2 g).

MS: calc.for $C_{24}H_{40}N_2O_4$: 420.3; Found: (M+1), (M+Na).

Piperidine Intermediate 3:

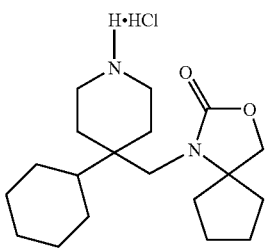

To the Intermediate 2 (1.2 g) was added hydrogen chloride (4.0 M in dioxane). The reaction mixture was stirred at room temperature for 30 minutes and the solvent was removed in vacuo to afford the title compound (1.2 g).

MS: calc.for $C_{19}H_{32}N_2O_2$: 320.3; Found: 321.1 (M+H).

Piperidine Intermediate 4:

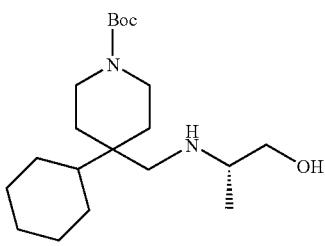

Intermediate 4 was prepared from (S)-(+)-2-amino-1-propanol in an analogous manner to the one described for the preparation of Intermediate 1.

MS: calc.for $C_{20}H_{38}N_2O_3$: 354; Found: 355 (M+H).

Piperidine Intermediate 5:

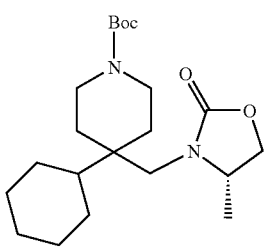

Intermediate 5 was prepared from Intermediate 4 in an analogous manner to the one described for the preparation of Intermediate 2.

MS: calc. for $C_{21}H_{36}N_2O_4$: 380.3; Found: 381 (M+H).

Piperidine Intermediate 6:

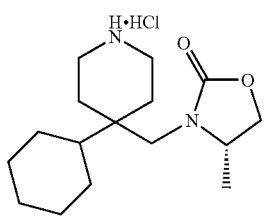

Intermediate 6 was prepared from Intermediate 5 in an analogous manner to the one described for the preparation of Intermediate 3.

MS: calc. for $C_{16}H_{28}N_2O_2$: 280.3; Found: 281 (M+).

Piperidine Intermediate 7:

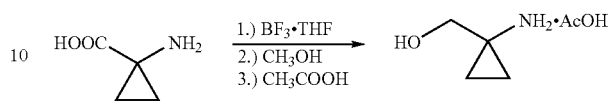

To a suspension of 1-aminocyclopropane-1-carboxylic acid (2.8 g, 27.7 mmol) in THF (20 ml) was added borane-tetrahydrofuran complex (100 ml, 100 mmol) slowly under nitrogen at room temperature. The reaction mixture was stirred at 70° C. overnight, then cooled to 0° C. After addition of methanol (12.2 ml, 300 mmol), the mixture was allowed to stir for 30 minutes. Then acetic acid (1.6 ml, 27.7 mmol) was added. The reaction mixture was concentrated to provide the title compound as a colorless oil (3.0 g).

Piperidine Intermediate 8:

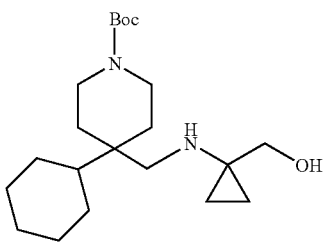

Intermediate 8 was prepared from Intermediate 7 in an analogous manner to the one described for the preparation of Intermediate 1.

MS: calc. for $C_{21}H_{38}N_2O_3$: 366.3; Found: 367 (M+H).

Piperidine Intermediate 9:

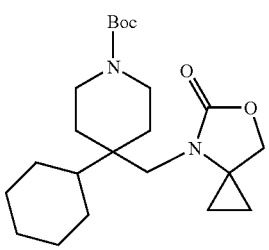

To a solution of Intermediate 8 (0.8 g, 2.18 mmol) in $CH_2Cl_2$ (40 ml) at 0° was added DMAP (0.266 g, 2.18 mmol), DIEA (1.52 ml, 8.74 mmol) and triphosgene (0.648 g, 2.18 mmol). After stirring the reaction mixture for one hour at 0° C., the ice-water bath was removed and the reaction mixture was allowed to stir at r.t. overnight. The mixture was diluted with $CH_2Cl_2$, washed with water and brine, dried over $MgSO_4$ and concentrated to give crude product, which was purified by column chromatography on silica gel (10% $CH_2Cl_2$/EtOAc) to give the title compound as a colorless oil (0.13 g).

ESI-MS: calc. for $C_{22}H_{36}N_2O_4$: 392; Found: 393 (M+1).

Piperidine Intermediate 10:

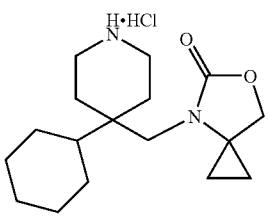

Intermediate 10 was prepared from Intermediate 9 in an analogous manner to the one described for the preparation of Intermediate 3.

MS: calc. for $C_{17}H_{28}N_2O_2$: 292.2; Found: 293 (M+H).

Piperidine Intermediate 11:

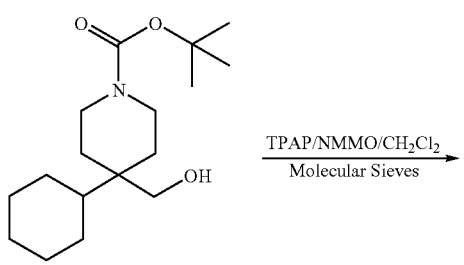

To a solution of the alcohol (9.41 g, 31.6 mmol) in $CH_2Cl_2$ (100 ml) at 0° C. containing molecular sieves (2 g) and 4-methylmorpholine N-oxide AMMO) (4.449 g, 37.98 mmol) was added TPAP (1.12 g, 3.16 mmol). After stirring the reaction mixture at 0° C. for 0.5 h, the reaction mixture was warmed to room temperature and stirred further for 5 hrs. The reaction mixture was concentrated to half the volume, diluted with hexane (250 ml), filtered through a silica gel pad and concentrated to give pure title compound (9.4 g).

Piperidine Intermediate 12:

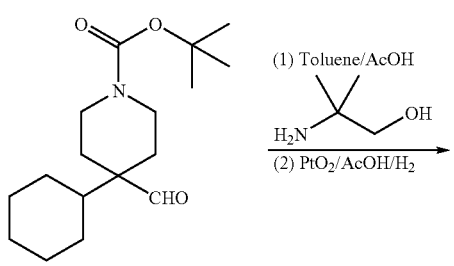

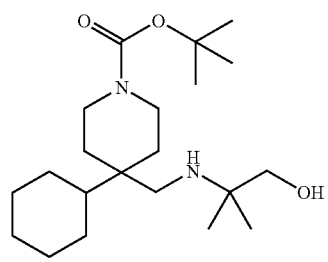

To a solution of the aldehyde (2 g, 6.7 mmol) in toluene (50 ml) was added acetic acid (500 µl). After stirring the reaction mixture at reflux temperature using Dean Stark apparatus for 8 hrs, the mixture was concentrated and dissolved in acetic acid (30 ml). To the mixture was added $PtO_2$ (500 mg) which was stirred under an atmosphere of $H_2$ overnight. The rection mixture was flushed with nitrogen, filtered and concentrated to give the title compound (2 g).

Piperidine Intermediate 13:

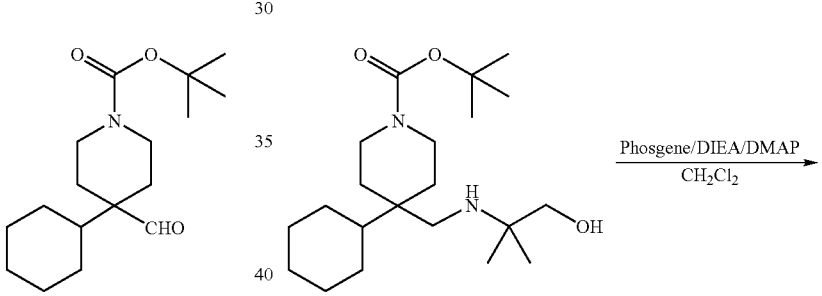

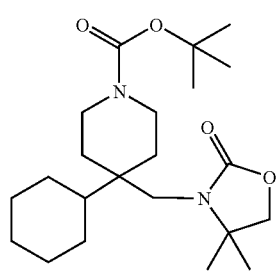

To a solution of the amino alcohol (4.96 g, 13.47 mmol) in $CH_2Cl_2$ at 0° C. containing DIEA (6.98 g, 53.9 mmol), DMAP (1.64 g, 13.47 mmol) was added slowly a toluene solution of phosgene (1.93M, 10.47 ml, 20.21 mmol). After stirring the reaction mixture for 1 hr at 0° C., the temperature was raised to room temperarure and stirred further for 2 hrs. The reaction mixture was diluted with $CH_2Cl_2$, washed with water, brine, dried and concentrated. The residue was purified by column chromatography over silica gel (5% EtOAc/$CH_2Cl_2$) to give pure product (3.95 g).

Piperidine Intermediate 14:

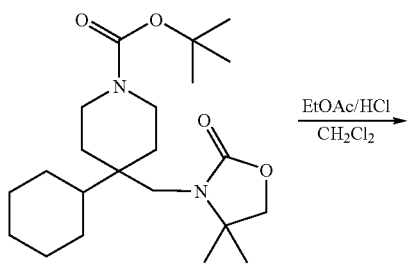

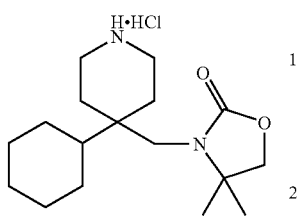

To a solution of Intermediate 13 (3.95 g) in CH$_2$Cl$_2$ was added 5 ml of a saturated HCl solution of EtOAc. After stirring the reaction mixture for 30 minutes at room temperature, the solvent was removed and the residue lyophilized from a benzene/methanol solution to afford the title compound (3.85 g).

Piperidine Intermediate 15:

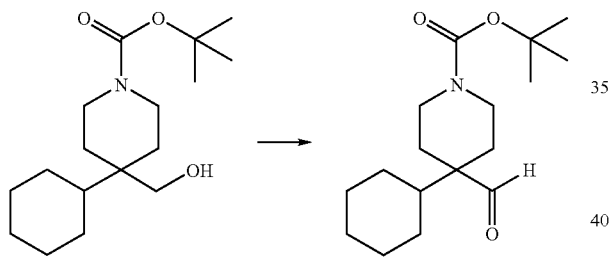

To a suspension of the alcohol (29 g, 97.5 mmol), 4-methylmorpholine-N-oxide (15.8 g, 134.6 mmol), and molecular sieves (15.0 gm) in DCM (500 mL) was added tetrapropylammonium perruthenate (TPAP, 1.03 g, 2.92 mmol) portionwise at room temperature. The mixture was stirred at room temperature for 30 min and TLC showed the reaction was completed. The mixture was filtered through a pad of silica gel, washed with DCM and 2:1 hexane/EtOAc. The mixture was then concentrated to give the aldehyde as a light yellow oil (28.5 g, 99%).

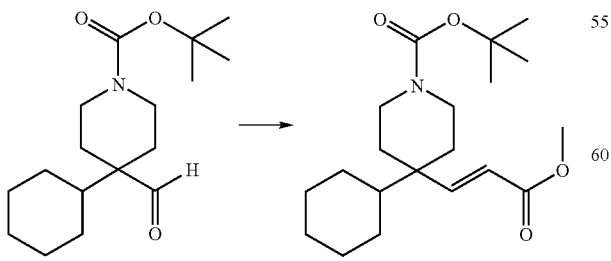

To a solution of methyl diethylphosphonoacetate (24.8 g, 117.8 mmol) in THF (400 mL) was add LDA (2.0 N, 58.9 mL, 117.8 mmol) at 0° C. After 30 min, a solution of the aldehyde from the previous step (28.5 g, 98.2 mmol) in THF (100 mL) was added, and the mixture was stirred at room temperature for two days and was then brought to reflux temperature overnight. The solvent was removed by rotary evaporation. The mixture was quenched with saturated NH$_4$Cl and extracted with EtOAc. The combined organic layers were washed with brine, dried, filtered, concentrated, and purified by medium pressure-liquid chromatography to give the unsaturated ester (31.3 g, 90.7%).

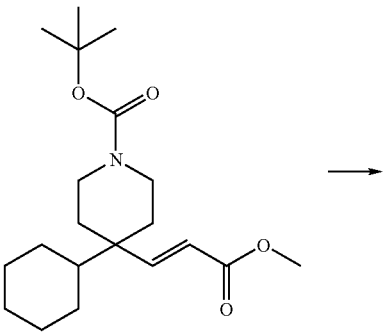

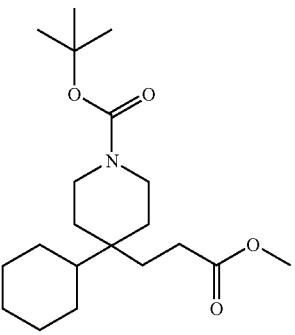

To a solution of the unsaturated ester (20 g, 56.9 mmol) in MeOH (200 mL) was added Pd/C (10%, 6.05 g), and the suspension was placed on a shaker under a hydrogen gas atmosphere (50 psi) overnight. The solid was filtered and washed with MeOH, and solvents were removed to give the product (19.3 g, 96%).

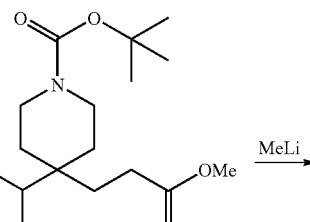

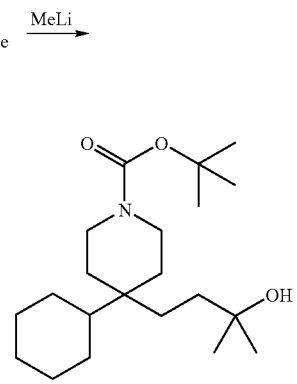

To a solution of the ester (2.9 g, 8.2 mmol) in dry THF (100 mL) was added MeLi (1.4 N in THF, 29.3 mL, 41.0 mmol) at −78° C. The mixture was stirred at −78° C. for 3 h and quenched with HCl (4.0 N in dioxane, 10.0 mL). The solvent was removed and the residue was washed with ether. The ether solution was concentrated to give the product (2.85 g, 98%) as an oil.

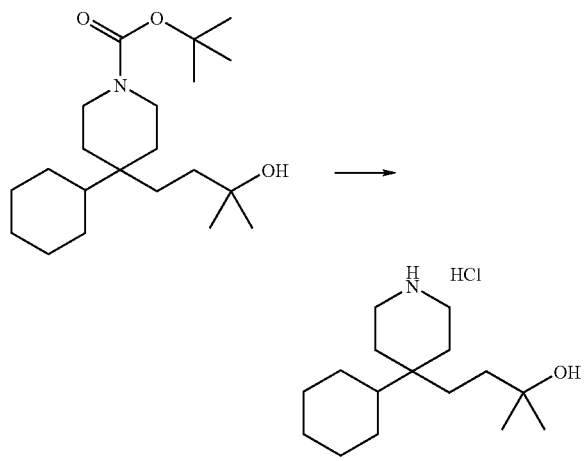

To a solution of HCl in dioxane (4 N, 14.1 mL, 56.6 mmol) was added the N-Boc-protected alcohol (2.0 g, 5.66 mmol) at room temperature. The mixture was stirred for 1 h and then the solution was evaporated to give Intermediate 15 (1.34 g, 81.7%) as a white solid.

Piperidine Intermediate 16:

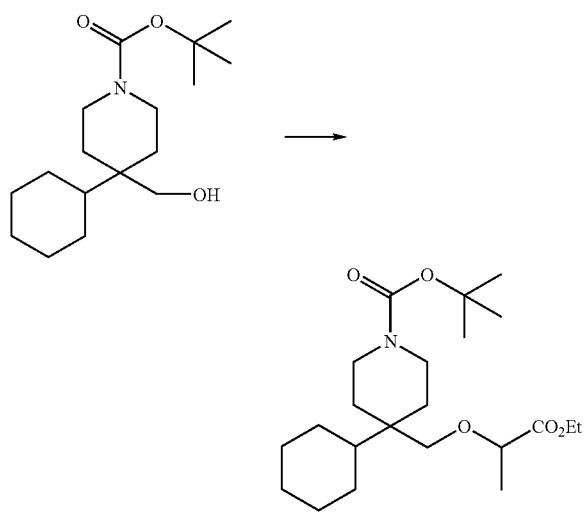

A dry flask was charged with NaH (60% in oil, 960 mg, 24 mmol) and anhydrous THF (40 mL). Added the alcohol starting material (5.95 g, 20 mmol) in dry THF (20 ml) through a two-ended needle under nitrogen atmosphere. Stirred at room temperature for about 60 min or until bubbling ceased, then added ethyl 2-bromoisopropionate (3.12 ml, 24 mmol). The mixture was stirred at room temperature overnight under nitrogen atmosphere. Quenched the reaction by adding the reaction mixture in portions to EtOAc (200 ml)/ice water (50 ml) with stirring. Transferred the mixture to a separatory funnel and added 1N HCl (30 ml). Extracted the aqueous solution with EtOAc (3×150 ml). Combined the organic phases which were dried over MgSO$_4$. Concentrated in vacuo and purified by flash column chromatography on silica gel using 20% EtOAc in hexane as eluent to give the desired product (1.0 g, 13%). LC-MS: M+1=398.5.

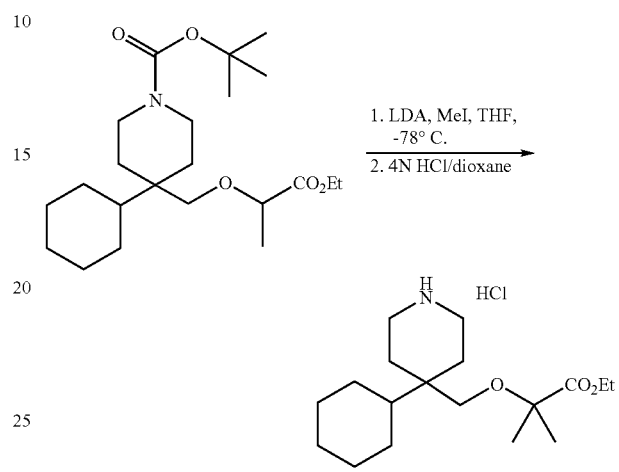

To the stirred solution of the Boc-derivative (1.0 g, 2.5 mmol) in dry THF (50 ml) was added LDA (1.5 M in cyclohexane, 2.0 ml, 3 mmol) dropwise at −78° C. The mixture was stirred at −78° C. for 30 min, then MeI (784 µl, 12.5 mmol) was added. Slowly warmed up to room temperature and stirred at room temperature overnight. Quenched the reaction by adding the reaction mixture in portions to EtOAc (200 ml)/ice water (50 ml) with stirring. Transferred the mixture to a separatory funnel and added 1N HCl (30 ml). Extracted the aqueous solution with EtOAc (3×150 ml). Combined the organic phases and dried over MgSO$_4$. Concentrated in vacuo and purified by flash column chromatography on silica gel using 20% EtOAc in hexane as eluent to give the desired product as a thick oil (681.8 mg). LC-MS: M+1=412.

$^1$H NMR (400 MHz, CDCl$_3$): δ 4.13 (q, J=7.2, 2H), 3.52 (br, 2H), 3.25 (s, 2H), 3.18–3.12 (m, 2H), 1.75–1.61 (m, 5H), 1.53–1.388 (m, 4H), 1.42 (s, 9H), 1.35 (s, 6H), 1.27 (t, J=7.2, 3H), 1.10 (m, 6H).

Dissolved the above resulting compound in 4N HCl in dioxane (20 ml). Stirred at room temperature for about 60 min. Evaporated to dryness to give Intermediate 16 as a white solid (541 mg). LC-MS: M+1=312.

Piperidine Intermediate 17:

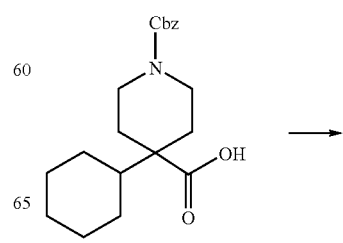

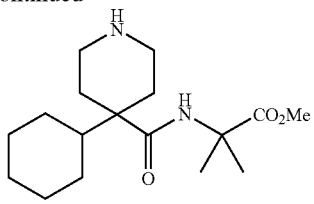

To the stirred solution of N-Cbz-4-cyclohexyl-piperidine-4-carboxylic acid (1.0 g, 2.9 mmol) in DCM (20 ml) was added oxalyl chloride (2.0M in DCM, 1.6 ml, 3.19 mmol) dropwise. Then added 3 drops of DMF. Stirred at room temperature for 1 hour and then evaporated to give the desired product. The crude mixture was used in the next step without further purification.

To the stirred solution of the acid chloride (2.9 mmol) in 1,2-dichloroethane (30 ml) was added α-methylalanine methyl ester (446 mg, 2.9 mmol) and DIEA (1.01 ml, 5.8 mmol). Stirred at 75° C. for 1 hour, and then at 60° C. overnight. Cooled to room temperature and diluted the mixture with DCM. Washed with 1N HCl, satd. NaHCO₃ and then satd. NaCl. Dried over Na₂SO₄ and concentrated in vacuo to give the crude desired product (1.2 g). LC-MS: 445 (M+1).

Dissolved intermediate from previous step (1.2 g, 2.7 mmol) in ethanol (50 ml). Added Pd-C (10%, 200 mg) and stirred at room temperature in the presence of hydrogen gas for two hours. Filtered off the catalyst, and concentrated in vacuo to give Intermediate 17 (663 mg). LC-MS: 312 (M+1).

Piperidine Intermediate 18:

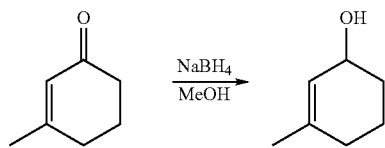

To a solution of the enone (6 mmol, 0.7 mL) in MeOH (20 mL) at 0° C. was added NaBH₄ (3 mmol, 113 mg). The reaction was stirred at room temp for 1 hr. Volatiles were removed and the residue partitioned between CH₂Cl₂ and 0.5M HCl. Organic phase was dried over MgSO₄ and concentrated to afford a clear colorless oil which was used in the next step without further purification.

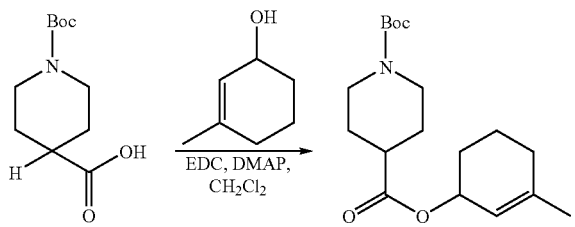

A solution of the acid (6 mmol, 1.38 g), EDC (12 mmol, 2.3 g), DMAP (ca.50 mg) and enol (ca. 6 mmol) in CH₂Cl₂ (25 mL) was stirred at room temp for 72 hours. Reaction mixture was poured into EtOAc (200 mL) and washed successively with 0.5M HCl, 1M NaOH, H₂O and brine, dried over Na₂SO₄ and concentrated. Chromatography over silica gel eluting with 500 mL of 5–10% EtOAc/hexane afforded a clear colorless oil (1.9 g).

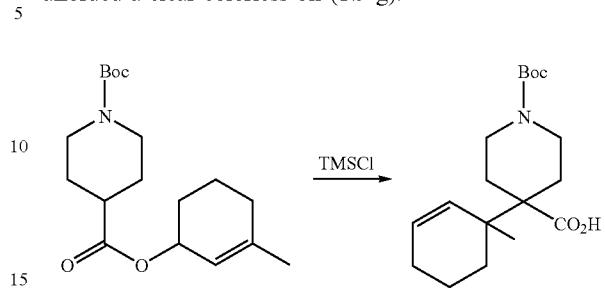

To a solution of LDA (2M in THF) (4.38 mmol, 2.2 mL) in THF (10 mL) at −78° C. was added the ester from the previous step (3.98 mmol, 1.3 g) in THF (2 mL) followed 30 min later by TMSCl (4.38 mmol, 0.6 mL). Resultant solution was allowed to warm to room temperature and then heated at reflux for 16 hr. After cooling to room temp, 2M HCl (5 mL) was added and stirring continued for 5 min. Resultant solution was partitioned between Et₂O (40 mL) and 2M HCl. The organic phase was washed with H₂O and brine, dried over Na₂SO₄ and concentrated. Chromatography over silica eluting with 20–30% EtOAc/hexane afforded the desired acid as an off-white solid (653 mg).

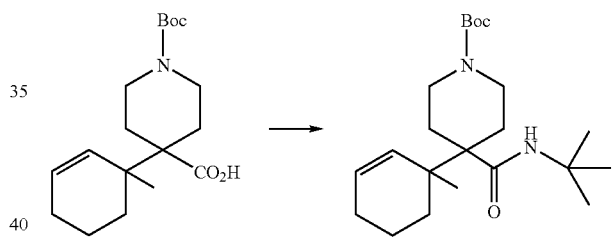

To a solution of the acid from the previous step (1.46 mmol, 474 mg) in CH₂Cl₂ (5 mL) at 0° C. was added oxalyl chloride (2M in CH₂Cl₂) (1.61 mmol, 0.81 mL) and DMF (0.05 mL) and the reaction stirred at 0° C. for 1 hr. Volatiles were removed, azeotroping with toluene and finally under high vacuum for 3 hr to afford the acid chloride. The acid chloride was dissolved in t-butylamine (5 mL) and the resultant cloudy solution was stirred at room temperature overnight. The reaction mixture was concentrated to afford a yellow solid. Chromatography over silica gel eluting with 50 mL of 5% then 100 mL of 10–20% EtOAc/hexane afforded the desired tert-butyl amide as a white solid (282 mg).

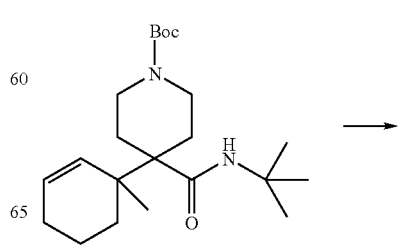

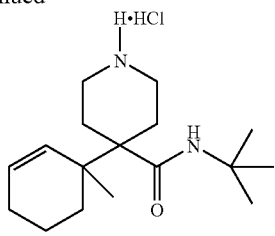

A suspension of Pd (10% on activated charcoal) (10 mol %, 79 mg) in a solution of the N-Boc derivative from the previous step (0.75 mmol, 282 mg) in MeOH containing 4M HCl (4M in dioxane) (1.5 mmol, 0.37 mL) was shaken under 45 psi of hydrogen gas for 60 hours. After work-up, the hydrochloride salt was used without further purification in the peptide coupling reaction.

Piperidine Intermediate 19:

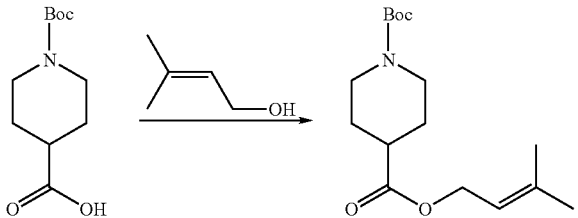

To a solution of the acid (10 mmol, 2.29 g) in CH$_2$Cl$_2$ (40 mL) at room temp was added EDC (20 mmol, 3.8 g) and DMAP (ca.50 mg) followed by 3-methyl-2-buten-1-ol (15 mmol, 1.52 mL). Resultant solution was stirred at room temp overnight. Reaction mixture was poured into EtOAc (200 mL) and washed successively with 0.5M HCl, 1M NaOH, H$_2$O and brine, dried over Na$_2$SO$_4$ and concentrated. Chromatography over silica gel eluting with 500 mL of 5% then 250 mL of 10% EtOAc/hexane afforded the ester as a clear colorless oil (2.97 g).

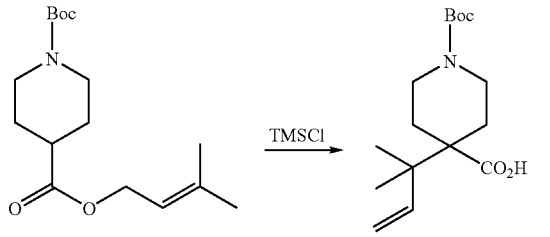

To a solution of LDA (2M in THF) (7.46 mmol, 3.73 mL) in THF (15 mL) at −78° C. was added the ester from the previous step (6.78 mmol, 2.02 g) in THF (3 mL) followed 30 min later by TMSCl (7.46 mmol, 0.95 mL). Resultant solution was allowed to warm to room temp and heated at reflux for 24 hr. After cooling to room temp, 2M HCl (5 mL) was added and stirring continued for 5 min. Resultant solution was partitioned between Et$_2$O (40 mL) and 2M HCl. The organic phase was washed with H$_2$O and brine, dried over Na$_2$SO$_4$ and concentrated. Chromatography over silica eluting with 10–20% EtOAc/hexane afforded the desired acid as a white solid (1.23 g).

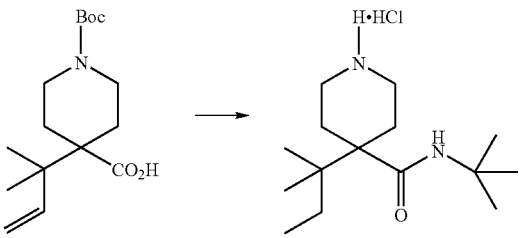

To a solution of the acid from the previous step (4.14 mmol, 1.23 g) in CH$_2$Cl$_2$ (10 mL) at 0° C. was added oxalyl chloride (2M in CH$_2$Cl$_2$) (4.55 mmol, 2.27 mL) and DMF (0.15 mL) and the reaction stirred at 0° C. for 1 hr. Volatiles were removed, azeotroping with toluene and finally under high vacuum for 3 hr to afford the acid chloride. The acid chloride was dissolved in t-butylamine (10 mL) and the resultant cloudy solution was left to stir at room temperature overnight. The reaction mixture was concentrated and partitioned between CH$_2$Cl$_2$ and 2M HCl. Organics were dried over Na$_2$SO$_4$ and concentrated. Chromatography over silica gel eluting with 10–30% EtOAc/hexane afforded a white solid (1.07 g).

A suspension of Pd (10% on activated charcoal) (10 mol %, 322 mg) in a solution of the compound from the previous step (3.03 mmol, 1.07 g) in MeOH (60 mL) containing 4M HCl in dioxane (6.06 mmol, 1.5 mL) was shaken under 45 psi of hydrogen gas for 5 hr. Reaction was filtered through a short pad of celite and concentrated. Residue was dissolved in EtOAc (20 mL) and HCl (4M in dioxane) (20 mL). Resultant solution was left to stir at room temp for 1 hr. Volatiles were removed and the residue precipitated from a CH$_2$Cl$_2$ solution with Et$_2$O/hexane to afford Intermediate 19 as a white solid.

Piperidine Intermediate 20:

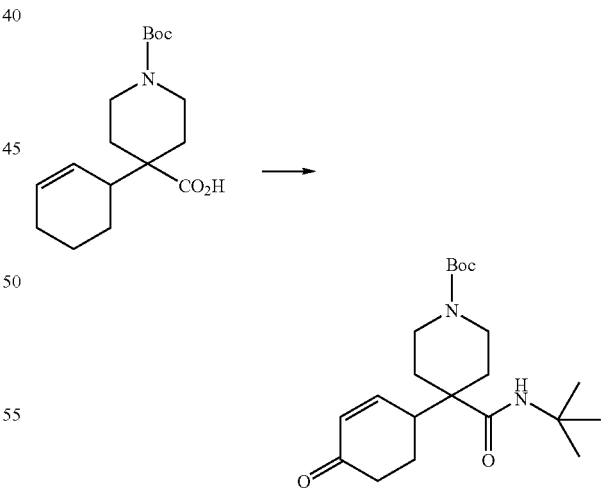

To a solution of CrO$_3$ (15.8 mmol, 1.59 g) in dry CH$_2$Cl$_2$ (20 mL) at −20° C. was added 3,5-dimethylpyrazole (15.8 mmol, 1.52 mg) in one portion. The resultant solution was stirred at −20° C. for 15 min before the addition of the cyclohexene intermediate (0.79 mmol, 289 mg) in CH$_2$Cl$_2$ (2.5 mL) over 3 min. The reaction mixture was warmed to −15° C. and stirred for a further 5 hr. 5N NaOH (51.5 mmol, 10.3 mL) was added and the emulsion stirred at 0° C. for 1 hr then at rt overnight. Aqueous phase was extracted with CH₂Cl₂, and the combined organics were washed with 1N HCl, water, satd NaHCO₃ and brine, dried over Na₂SO₄ and concentrated. Chromatography over silica gel eluting with 50 mL of 0, 2.5, 5, and 10% EtOAc/hexane afforded the cyclohexenone as a white solid (135 mg).

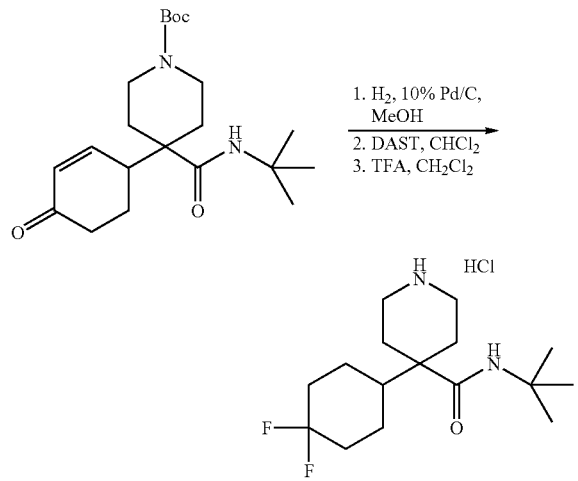

A suspension of Pd (10% on activated charcoal) (20 mol %, 76 mg) in a solution of the cyclohexenone (0.36 mmol, 135 mg) in MeOH was shaken under 45 psi of hydrogen gas for 60 hr. The reaction mixture was filtered through a short pad of celite and concentrated to afford a clear colorless gum. Chromatography over silica gel eluting with 50 mL of 0, 2.5, 5, 10, and 20% Me₂CO/CH₂Cl₂ afforded the cyclohexanone as a white solid (111 mg).

To a solution of the cyclohexanone (0.29 mmol, 111 mg) in CH₂Cl₂ was added (diethylamino)sulfur trifluoride (0.73 mmol, 0.1 mL). Resultant solution was left to stir at room temp for 24 hours. Reaction mixture was poured into saturated NaHCO₃. Organic phase was washed with NaHCO₃, dried over Na₂SO₄ and concentrated. Chromatography over silica gel eluting with 10–30% EtOAc/hexane afforded the difluorocyclohexane intermediate as a white solid (84 mg)

A solution of the difluorocyclohexane intermediate from the previous step (0.2 mmol, 80 mg) in CH₂Cl₂ and TFA was stirred at room temp for 1 hr. Volatiles were removed and the residue partitioned between NaOH and EtOAc. Organic phase was dried over Na₂SO₄ and concentrated to give Intermediate 20.

Piperidine Intermediate 21:

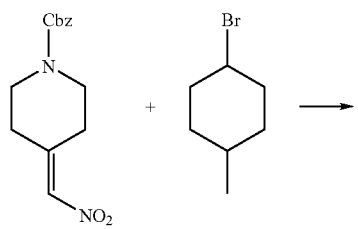

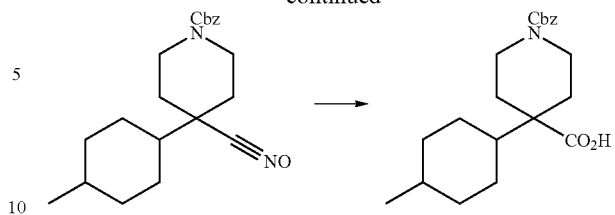

To a suspension of Reike Mg (5 g/200 mL THF) (6 mmol, 6 mL) at 0° C. was added a solution of 4-methyl-1-bromocyclohexane (4 mmol, 708 mg) in THF (4 mL) over a period of about 5 min. The resultant slurry was stirred at room temp for 5 min then cooled to −20° C. A solution of the Cbz-piperidine derivative (1 mmol, 276 mg) in THF (10 mL) was then added. The reaction was stirred at −20° C. for 15 min then poured into ice-cold 50% H₂SO₄ (25 mL) and stirred for a further 30 min. The emulsion was poured into H₂O (100 mL) and extracted with CH₂Cl₂ (2×25 mL). The combined organic phases were dried over Na₂SO₄ and concentrated to afford a green oil. To a solution of this oil in DMSO (2 mL) was added NaNO₂ (3 mmol, 207 mg) and AcOH (10 mmol, 0.6 mL). The resultant orange solution was stirred at 40° C. for 24 hr. After cooling to room temperature, 1N HCl (2.5 mL) was added and stirring continued for a further 15 min. The mixture was extracted with CH₂Cl₂ (3×5 mL). The combined organic layers were dried over Na₂SO₄ and concentrated. Chromatography over silica gel eluting with 100 mL of 10% and 50 mL of 20–30% EtOAc/hexane afforded the desired acid as an off-white solid (100 mg).

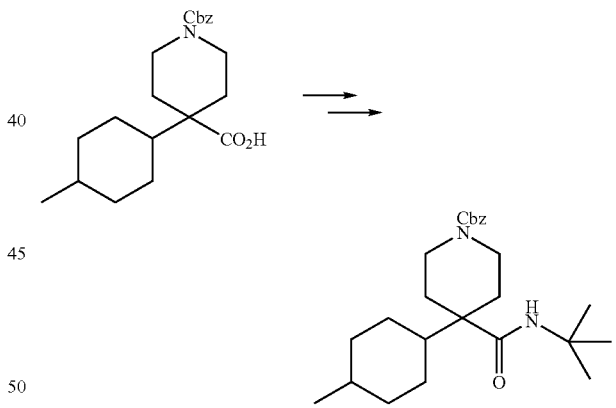

To a solution of the acid (0.42 mmol, 151 mg) in CH₂Cl₂ (2.5 mL) at 0° C. was added oxalyl chloride (2M in CH₂Cl₂) (0.46 mmol, 0.23 mL) and DMF (4 drops) and the reaction stirred at 0° C. for 1 hr. Volatiles were removed, azeotroping with toluene and finally under high vacuum for 3 hr to afford the acid chloride. The acid chloride was dissolved in CH₂Cl₂ (2.5 mL) and cooled to 0° C. t-Butylamine (1.26 mmol, 0.13 mL) was added and the resultant cloudy solution was left to stir at room temperature overnight. The reaction mixture was poured into CH₂Cl₂ (ca. 3 mL) and washed with brine, dried over Na₂SO₄ and concentrated. Chromatography over silica gel eluting with 250 mL of 20, 25, 30, and 40% EtOAc/hexane afforded the Cbz-protected t-butyl amide as a white foam (174 mg). A mixture of the Cbz-protected t-butyl amide (0.1 mmol, 174 mg) and catalytic Pd (10% on activated C) (20 mg) in methanol was stirred under an atmosphere of hydrogen gas at room temp for 1 hr. The solution was filtered through a short pad of celite and concentrated to give Intermediate 21.

Piperidine Intermediate 22:

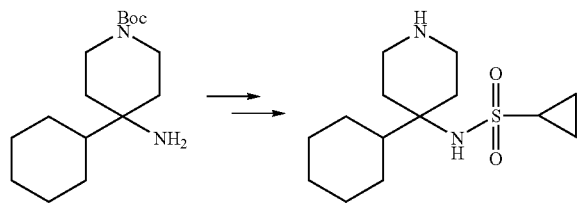

A solution of the amine (400 mg, 1.42 mmol), cyclopropylsulfonyl chloride (600 mg, 4.26 mmol), DIEA (1.47 g, 11.36 mmol) and DMAP (100 mg, 0.8 mmol) in toluene (50 mL) was heated to reflux overnight. A solution of NaOH (5N, 10 mL) was added and allowed the reaction to reflux for an additional 4 h. The reaction mixture was cooled to rt and diluted with EtOAc (200 mL). The combined organics were washed with 0.5N HCl, satd NaHCO$_3$, and brine, dried over Na$_2$SO$_4$ and concentrated. Chromatography over silica gel eluting with 50 mL of 10, 20, 15, 25, 40, and 50% EtOAc/hexane afforded the Boc-protected intermediate as a white solid (615 mg). A solution of this intermediate in CH$_2$Cl$_2$ (4 mL) and HCl (4M in dioxane) (4 mL) was stirred at room temp for 1 hr. Volatiles were removed and the product precipitated from a CH$_2$Cl$_2$ solution with Et$_2$O/hexane to give Intermediate 22 (615 mg).

Piperidine Intermediate 23:

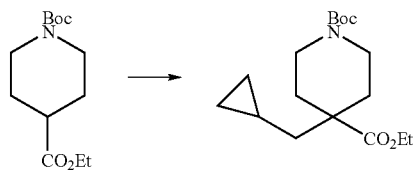

To a solution of the ester (2.36 g, 9.17 mmol) in THF (50 mL) at −78° C. was added LDA (1.5M in 1) (6.72 mL, 10.09 mmol) and followed 45 min later by cyclopropylmethyl bromide (1.49 g, 11.0 mmol) in THF (10 mL). Resultant solution was allowed to warm to room temp overnight. Resultant solution was quenched with sat. NH$_4$Cl and partitioned between EtOAc (40 mL) and 0.5M HCl. The organic phase was washed with H$_2$O and brine, dried over Na$_2$SO$_4$ and concentrated. Chromatography over silica gel eluting with 5% EtOAc/hexane afforded the alkylated product (2.76 g).

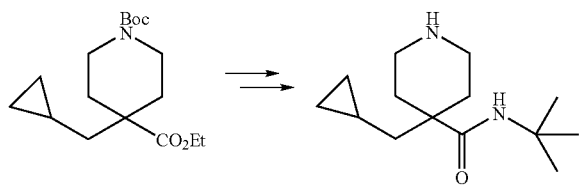

A solution of intermediate from the previous step (2.76 g, 8.86 mmol) and LiOH (1.1 g, 44.3 mmol) in MeOH/H$_2$O (70 mL) was heated to reflux overnight. More MeOH was added to the reaction mixture to make the solution homogeneous. The reaction mixture was concentrated to about 10 mL and acidified with 2N HCl to pH about 2. The aqueous solution was extracted with EtOAc (3×100 mL). The organics were washed successively with H$_2$O and brine, dried over Na$_2$SO$_4$ and concentrated. Chromatography over silica gel eluting with 20–70% EtOAc/hexane afforded the Boc-protected acid as a white solid (1.69 g). To a solution of the acid (2.5 g, 8.82 mmol) in CH$_2$Cl$_2$ (5 mL) at 0° C. was added oxalyl chloride (2M in CH$_2$Cl$_2$) (4.85 mL, 9.70 mmol) and DMF (0.05 mL) and the reaction stirred at 0° C. for 1 hr. Volatiles were removed, azeotroping with toluene and finally under high vacuum for 3 hr to afford the acid chloride. The acid chloride was dissolved in t-butylamine (2.8 mL), and the resultant cloudy solution was left to stir at room temp overnight. The reaction mixture was concentrated and partitioned between CH$_2$Cl$_2$ and 2M HCl. Organics were dried over Na$_2$SO$_4$ and concentrated. A solution of the Boc-protected amide in CH$_2$Cl$_2$ (4 mL) and 4.0 M HCl/dioxane (4 mL) was stirred at room temp for 1 hr. Volatiles were removed and Intermediate 23 was precipitated from a CH$_2$Cl$_2$ solution with Et$_2$O/hexane (1.9 g).

Piperidine Intermediate 24:

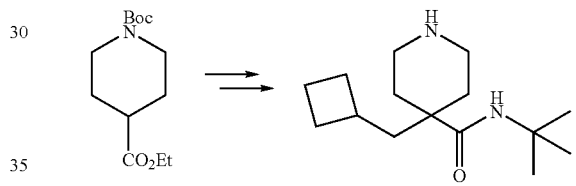

This intermediate was prepared in the same manner as Intermediate 23 but using cyclobutylmethyl bromide in place of cyclopropylmethyl bromide in the alkylation step.

Piperidine Intermediate 25:

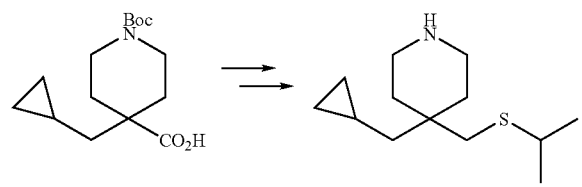

To a solution of the acid (600 mg, 2.117 mmol) in THF (5 mL) at 0° C. was added BH$_3$.Me$_2$S (10 M in THF) (0.85 mL, 8.47 mmol) and the solution was left to stir at room temperature for 3 h. The reaction mixture was then cooled to 0° C., and H$_2$O$_2$ (30% aqueous, 2.5 mL) was added dropwise and then 1M NaOH (10 mL). The resultant solution was stirred for 10 min at 0° C. and then a further 30 min at rt. The reaction mixture was poured into EtOAc (100 mL), and washed successively with water, sat. NH$_4$Cl, saturated NaHCO$_3$, and brine, dried over Na$_2$SO$_4$ and concentrated. Chromatography over silica gel eluting with 40% EtOAc/hexane afforded the alcohol intermediate (611 mg). To a solution of the alcohol (611 mg, 2.268 mmol) and Et$_3$N (0.63 mL, 4.5 mmol) in CH$_2$Cl$_2$ (5 mL) at 0° C. was added methanesulfonyl chloride (10 M in THF) (0.35 mL, 4.53 mmol) at 0° C. and the solution was left to stir at room temp 45 min. The reaction was concentrated and was poured into water (100 mL), and extracted with EtOAc (3×100 mL). The organics were dried over Na₂SO₄ and concentrated. Chromatography over silica gel eluting with 5–30% EtOAc/hexane afforded the mesylate as a solid. To a solution of the mesylate (596 mg, 1.7 mmol) in DMF (5 mL) at rt was added sodium isopropylsulfide (842 mg, 8.57 mmol) and the solution was left to stir at room temp overnight. The reaction was concentrated and was poured into water (100 mL), and extracted with EtOAc (3×100 mL). The organics were dried over Na₂SO₄ and concentrated. Chromatography over silica gel eluting with 5–30% EtOAc/hexane afforded a solid. A solution of the Boc-protected isopropyl sulfide in CH₂Cl₂ (4 mL) and 4.0 M HCl/dioxane (4 mL) was stirred at room temp for 1 hr. Volatiles were removed and Intermediate 25 was precipitated from a CH₂Cl₂ solution with Et₂O/hexane (400 mg).

Piperidine Intermediate 26:

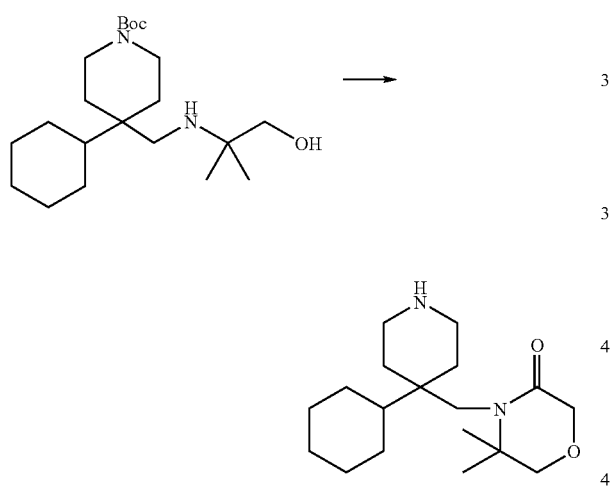

To a solution of the amino alcohol (177 mg, 0.48 mmol), NaOH (192 mg, 4.8 mmol) in CHCl₃ (5 mL) and water (2 mL) at 0° C. was added dropwise a solution of BrCH₂COBr (263 mg, 1.3 mmol) in CHCl₃ (1 mL) over a period of 5 min., and the solution was left to stir at 0° C. for 1 h and then at rt overnight. The reaction was concentrated and was poured into water (100 mL), and extracted with EtOAc (3×100 mL). The organics were washed successively with water, 1N HCl and brine and dried over Na₂SO₄ and concentrated. Chromatography over silica gel eluting with 25% EtOAc/hexane afforded a solid. A solution of this solid in CH₂Cl₂ (4 mL) and 4.0 M HCl/dioxane (4 mL) was stirred at room temp for 1 hr. Volatiles were removed and Intermediate 26 precipitated from a CH₂Cl₂ solution with Et₂O/hexane (100 mg).

The following Examples are provided to illustrate the invention and are not to be construed as limiting the scope of the invention in any manner.

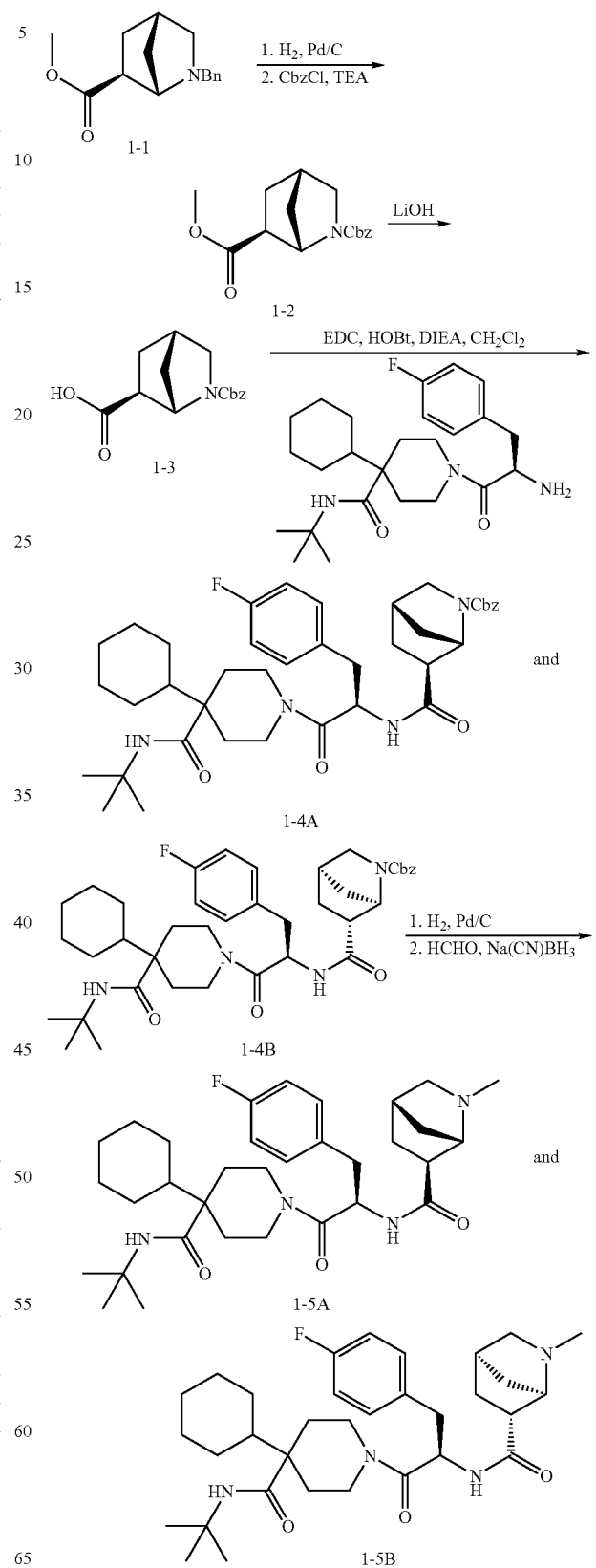

Scheme 1

EXAMPLE 1

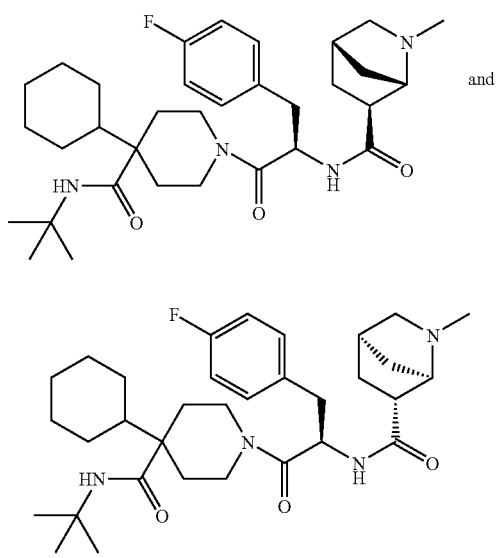

Step A:
To a solution of compound 1-1 (10 g, 41 mmol, Maybridge, BTBG 0121) in 50 mL of methanol was added palladium on carbon (0.41 g). The mixture was stirred at r.t. under hydrogen gas (1 atmosphere) overnight. The solid was filtered and washed with methanol. The filtrates were concentrated to give 1-1 as colorless oil (6.3 g).

ESI-MS: Calcd for $C_9H_{13}NO_2$: 155; Found: 156 (M$^+$+1).

Step B:
To a solution of compound 1-1' (6.3 g, 41 mmol) in 50 mL of THF were added TEA (6.8 mL, 49 mmol) and benzyl chlorofomate (7.6 g, 45 mmol). The reaction mixture was stirred at r.t. overnight. The reaction mixture was diluted with ethyl acetate and washed with 1N HCl and brine, dried over MgSO$_4$, filtered and concentrated to give compound 1-2 as an thick oil (11 g).

ESI-MS: Calcd. for $C_{16}H_{19}NO_4$: 289; Found: 290 (M$^+$+1).

Step C:
To a solution of compound 1-2 (11 g, 39 mmol) in 80 mL of THF was added a solution of lithium hydroxide (2.8 g, 119 mmol) in 20 mL of H$_2$O. The reaction mixture was stirred at r.t. overnight. The reaction mixture was concentrated and H$_2$O was added and then acidified by adding aqueous 1 N HCl solution until a pH of about 4 was achieved. The solution was extracted with EtOAc, and the combined organic extracts were washed with brine, dried over MgSO$_4$, filtered, and concentrated to give compound 1-3 as an off-white solid (7.2 g).

ESI-MS: Calcd. for $C_{15}H_{17}NO_4$: 275; Found: 276 (M$^+$+1).

Step D:
Acid 1-3 (0.59 g, 2.1 mmol) was dissolved in 10 mL of DMF, and then the 4-F-D-Phe-4-cyclohexyl-piperidine-4-carboxylic acid tert-butyl amide (1.0 g, 2.1 mmol), DIEA (0.83 g, 6.4 mmol), EDC (0.49 g, 2.6 mmol), and HOBt (0.35 g, 2.6 mmol) were added. The resulting mixture was stirred at r.t. overnight, and then diluted with ethyl acetate, and washed with 1N HCl solution, saturated NaHCO$_3$ solution, and brine. The organic layer was dried over MgSO$_4$, filtered, and concentrated. The isomers were separated by medium-pressure liquid chromatography (1:1 ethyl acetate-methylene chloride as eluant) to give 1-4A (diastereomer 1, 0.52 g) and 1-4B (diastereomer 2, 0.51 gm).

ESI-MS (1-4A diastereomer 1): Calcd. for $C_{40}H_{53}N_4O_5F$: 688; Found: 689 (M$^+$+1).

ESI-MS (1-4B diastereomer 2): Calcd. for $C_{40}H_{53}N_4O_5F$: 688; Found: 689 (M$^+$+1).

Step E:
To a solution of compound 1-4A (diastereomer 1, 0.52 g, 0.76 mmol) in 10 mL of methanol was added palladium-on-carbon (0.01 g). The mixture was stirred at r.t. under hydrogen gas (1 atmosphere) overnight. The solid was filtered and washed with methanol. The filtrates were concentrated to give 1-4A (diastereomer 1, 0.41 g).

ESI-MS: Calcd for $C_{32}H_{47}N_4O_3F$: 554; Found: 555 (M$^+$+1).

To a solution of compound 1-4B (diastereomer 2, 0.51 g, 0.74 mmol) in 10 mL of methanol was added Palladium on carbon (0.01 g). The mixture was stirred at r.t. under hydrogen gas (1 atmosphere) overnight. The solid was filtered and washed with methanol. The filtrates were concentrated to give 1-4B (diastereomer 2, 0.40 g).

ESI-MS: Calcd for $C_{32}H_{47}N_4O_3F$: 554; Found: 555 (M$^+$+1).

Step F:
To a solution of compound 1-4A (diastereomer 1, 0.11 g, 0.20 mmol) in 5 mL of methanol was added formaldehyde (0.20 mL, 37% in water, 2.0 mmol). After the mixture was stirred for 30 min, a solution of NaCNBH$_3$ (1.0 mL, 1.0 M, 1.0 mmol) was added. The mixture was then stirred at r.t. overnight and solvents were removed under reduced pressure. The residue was quenched with sat'd NaHCO$_3$ and extracted with EtOAc. The combined organic layers were washed with brine, dried over MgSO$_4$, filtered, and concentrated to give 1-5A (diastereomer 1, 0.097 g).

ESI-MS: Calcd for $C_{33}H_{49}N_4O_3F$: 568; Found: 569 (M$^+$+1).

To a solution of compound 1-4B (diastereomer 2, 0.11 g, 0.20 mmol) in 5 mL of methanol was added formaldehyde (0.20 mL, 37% in water, 2.0 mmol). After the mixture was stirred for 30 min, a solution of NaCNBH$_3$ (1.0 mL, 1.0 M, 1.0 mmol) was added. The mixture was then stirred at r.t. overnight and solvents were removed under reduced pressure. The residue was quenched with sat'd NaHCO$_3$ and extracted with EtOAc. The combined organic layers were washed with brine, dried over MgSO$_4$, filtered, and concentrated to give 1-5B (diastereomer 2, 0.097 g).

ESI-MS: Calcd for $C_{33}H_{49}N_4O_3F$: 568; Found: 569 (M$^+$+1).

The following Examples shown in Table 1 having the indicated R stereochemistry at the stereogenic center marked with an * and the indicated anti stereochemistry at the stereogenic center marked with an ** relative to the [2.2.1]-bicycle ring nitrogen were prepared in a similar fashion as Example 1 following the methodologies shown in Schemes A and B.

TABLE 1

| Ex. | X | R⁶ | Diastereomer with antistereo-chem at ** | R⁵ | Mass spectrum |
|---|---|---|---|---|---|
| 2 | -C(O)OEt | Cl | d₁ | H | 544 (M⁺ + 1) |
| 3 | -C(O)OEt | Cl | d₂ | H | 544 (M⁺ + 1) |
| 4 | -C(O)OEt | F | d₁ + d₂ | H | 528 (M⁺ + 1) |
| 5 | -C(O)OEt | F | d₁ + d₂ | iPr | 570 (M⁺ + 1) |
| 6 | -C(O)NH-tBu | F | d₁ | H | 555 (M⁺ + 1) |
| 7 | -C(O)NH-tBu | F | d₂ | H | 555 (M⁺ + 1) |
| 8 | -C(O)NH-tBu | F | d₁ | iPr | 597 (M⁺ + 1) |
| 9 | -C(O)NH-tBu | F | d₂ | iPr | 597 (M⁺ + 1) |

Scheme 2

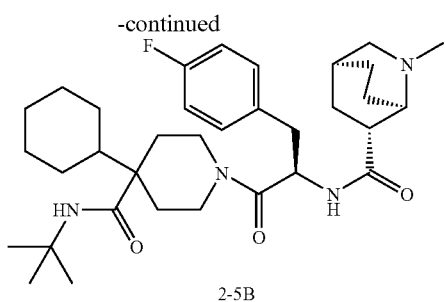

2-5B

EXAMPLE 10

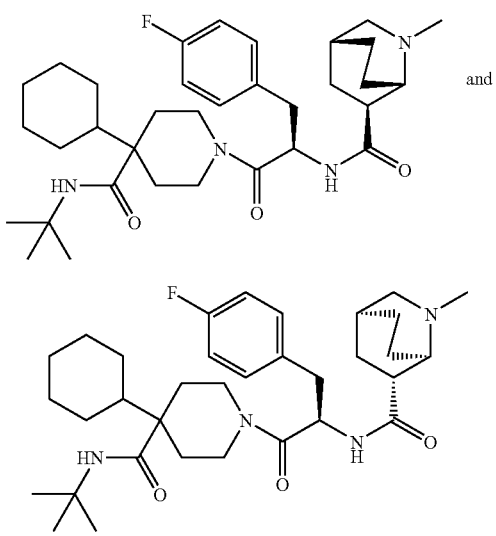

Step A:

To a solution of compound 2-1 (1.0 g, 3.6 mmol) [for preparation of 2-1, see *Tetrahedron*, 48: 8751 (1992) and *J. Med. Chem.*, 33: 2690 (1996)] in 10 mL of methanol was added palladium-on-carbon (0.035 g). The mixture was stirred at r.t. under hydrogen gas (1 atmosphere) overnight. The solid was filtered and washed with methanol. The filtrates were concentrated to give 2-2 as a colorless oil (0.95 g).

ESI-MS: Calcd for $C_{14}H_{23}NO_4$: 269; Found: 270 (M$^+$+1).

Step B:

To a solution of compound 2-2 (0.95 g, 3.5 mmol) in 15 mL of THF was added a solution of lithium hydroxide (0.5 g, 23 mmol) in 5 mL of H$_2$O. The reaction mixture was stirred at r.t. overnight. The reaction mixture was concentrated and H$_2$O was added and then acidified by adding aqueous 1 N HCl solution until a pH of about 4 was achieved. The solution was extracted with EtOAc, and the combined organic extracts were washed with brine, dried over MgSO$_4$, filtered, and concentrated to give compound 2-3 as a white solid (0.78 g).

ESI-MS: Calcd. for $C_{13}H_{21}NO_4$: 255; Found: 256 (M$^+$+1).

Step C:

Acid 2-3 (0.55 g, 2.1 mmol) was dissolved in 30 mL of methylene chloride, and then the 4-F-D-Phe-4-cyclohexyl-piperidine-4-carboxylic acid tert-butyl amide (1.0 g, 2.1 mmol), DIEA (0.37 mL, 2.1 mmol), EDC (0.82 g, 4.2 mmol), and HOBt (0.29 g, 2.1 mmol) were added. The resulting mixture was stirred at r.t. overnight, and then diluted with methylene chloride, and washed with 1N HCl solution, saturated NaHCO$_3$ solution, and brine. The organic layer was dried over MgSO$_4$, filtered, and concentrated. The isomers were purified by flash chromatography on silica gel (2:3 EtOAc-hexane) to give 2-4A (diastereomer 1, 0.55 g) and 2-4B (diastereomer 2, 0.62 gm).

ESI-MS (1-4A): Calcd. for $C_{38}H_{57}N_4O_5F$: 668; Found: 669 (M$^+$+1).

ESI-MS (1-4B): Calcd. for $C_{38}H_{57}N_4O_5F$: 668; Found: 669 (M$^+$+1).

Step D:

Compound 2-4A (diastereomer 1, 0.52 g, 0.78 mmol) was dissolved in 10 mL of 4 N HCl in dioxane. This solution was stirred at r.t. for 60 min, and then concentrated to give 2-4A as a white solid (diastereomer 1, 0.48 g).

ESI-MS: Calcd for $C_{33}H_{49}N_4O_3F$: 568; Found: 569 (M$^+$+1).

Compound 2-4B (diastereomer 2, 0.43 g, 0.64 mmol) was dissolved in 10 mL of 4 N HCl in dioxane. This solution was stirred at r.t. for 60 min, and then concentrated to give 2-4B as a white solid (diastereomer 2, 0.39 g).

ESI-MS: Calcd for $C_{33}H_{49}N_4O_3F$: 568; Found: 569 (M$^+$+1).

Step E:

To a solution of compound 2-4A (diastereomer 1, 0.11 g, 0.18 mmol) in 2 mL of methylene chloride was added formaldehyde (0.15 mL, 37% in water, 1.8 mmol), DIEA (0.032 mL, 0.18 mmol), and molecular sieves (700 mg, 4A powder). After the mixture was stirred for 5 min, Na(OAc)$_3$BH (0.37 g, 1.8 mmol) was added and the mixture was then stirred at r.t. overnight. The mixture was diluted with methylene chloride, washed with saturated NaHCO$_3$, dried over NaSO$_4$, filtered, and concentrated to give 2-5A (diastereomer 1, 0.11 g).

ESI-MS: Calcd for $C_{34}H_{51}N_4O_3F$: 582; Found: 583 (M$^+$+1).

To a solution of compound 2-4B (diastereomer 2, 0.10 g, 0.17 mmol) in 2 mL of methylene chloride was added formaldehyde (0.13 mL, 37% in water, 1.7 mmol), D]EA (0.029 mL, 0.17 mmol), and molecular sieves (700 mg, 4A powder). After the mixture was stirred for 5 min, Na(OAc)$_3$BH (0.35 g, 1.7 mmol) was added and the mixture was then stirred at r.t. overnight. The mixture was diluted with methylene chloride, washed with sat'd NaHCO$_3$, dried over NaSO$_4$, filtered, and concentrated to give 2-5B (diastereomer 2, 0.085 g).

ESI-MS: Calcd for $C_{34}H_{51}N_4O_3F$: 582; Found: 583 (M$^+$+1).

The following Examples shown in Table 2 having the indicated R stereochemistry at the stereogenic center marked with an * and the indicated anti stereochemistry at the stereogenic center marked with an ** relative to the [2.2.2]-bicycle ring nitrogen were prepared in a similar fashion as Example 10 following the methodologies shown in Schemes A and B.

TABLE 2

| Ex. | X | R⁶ | Diastereomer with anti-stereochem at ** | R⁵ | Mass spectrum |
|---|---|---|---|---|---|
| 11 | ethyl ester (-C(O)OEt) | F | d₁ + d₂ | H | 542 (M⁺ + 1) |
| 12 | ethyl ester | F | d₂ | Me | 556 (M⁺ + 1) |
| 13 | ethyl ester | F | d₁ + d₂ | iPr | 584 (M⁺ + 1) |
| 14 | ethyl ester | F | d₁ + d₂ | cyclobutyl | 596 (M⁺ + 1) |
| 15 | ethyl ester | F | d₁ + d₂ | -C(O)CH(NH₂)CH₃ | 613 (M⁺ + 1) |
| 16 | ethyl ester | F | d₁ | —CH₂CO₂H | 600 (M⁺ + 1) |
| 17 | ethyl ester | F | d₁ | —CH₂CONH₂ | 599 (M⁺ + 1) |
| 18 | ethyl ester | F | d₁ | -C(O)CH(NH₂)CH₂OH | 763 (M⁺ + 1) |
| 19 | ethyl ester | F | d₁ | 4-methylimidazol-5-ylmethyl | 636 (M⁺ + 1) |

TABLE 2-continued
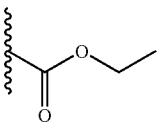
| Ex. | X | R⁶ | Diastereomer with anti-stereochem at ** | R⁵ | Mass spectrum |
|---|---|---|---|---|---|
| 20 | 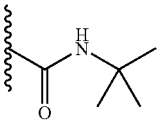 | F | d₁ | —COCH₂NH₂ | 599 (M⁺ + 1) |
| 21 | 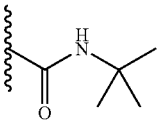 | F | d₁ + d₂ | H | 569 (M⁺ + 1) |
| 22 | 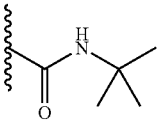 | Cl | d₁ + d₂ | Me | 583 (M⁺ + 1) |
| 23 | 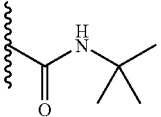 | Cl | d₁ + d₂ | iPr | 611 (M⁺ + 1) |
| 24 | 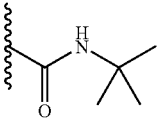 | F | d₁ + d₂ | cyclobutyl | 623 (M⁺ + 1) |
| 25 | 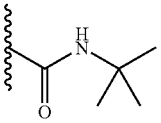 | F | d₁ | 2,2-difluoroethyl | 633 (M⁺ + 1) |
| 26 | 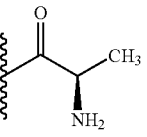 | F | d1 | 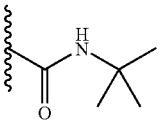 | 640 (M⁺ + 1) |
| 27 | 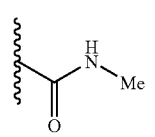 | Cl | d₁ + d₂ | H | 586 (M⁺ + 1) |
| 28 |  | Cl | d₁ + d₂ | H | 544 (M⁺ + 1) |

TABLE 2-continued

| Ex. | X | R⁶ | Diastereomer with anti-stereochem at ** | R⁵ | Mass spectrum |
|---|---|---|---|---|---|
| 29 | -OC(O)CH₂CH₂OMe (ester linkage) | F | d₁ + d₂ | H | 572 (M⁺ + 1) |
| 30 | CH₂-(1,2,4-triazol-1-yl) | Cl | d₁ + d₂ | H | 569 (M⁺ + 1) |
| 31 | CH₂-(1,2,4-triazol-1-yl) | F | d₁ + d₂ | iPr | 611 (M⁺ + 1) |
| 32 | CH₂-(4,4-dimethyl-2-oxo-oxazolidin-3-yl) | F | d₁ + d₂ | H | 614 (M⁺ + 1) |
| 33 | CH₂-(4,4-dimethyl-2-oxo-oxazolidin-3-yl) | F | d₁ | Me | 628 (M⁺ + 1) |
| 34 | CH₂C(O)NEt₂ | F | d₁ + d₂ | H | 583 (M⁺ + 1) |
| 35 | CH₂C(O)NEt₂ | F | d₁ + d₂ | cyclobutyl | 637 (M⁺ + 1) |
| 36 | NHC(O)tBu | F | d₁ + d₂ | Me | 583 (M⁺ + 1) |
| 37 | NHC(O)-(1-methylcyclopropyl) | F | d₁ + d₂ | Me | 581 (M⁺ + 1) |

Biological Assays:

A. Binding Assay. The membrane binding assay was used to identify competitive inhibitors of $^{125}$I-NDP-alpha-MSH binding to cloned human MCRs expressed in L- or CHO-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 ml 10% heat-inactivated fetal bovine serum (Sigma); 10 ml 10,000 unit/ml penicillin & 10,000 ug/ml streptomycin (Gibco/BR1); 10 ml 200 mM L-glutamine (Gibco/BR1); 1 mg/ml Geneticin (G418) (Gibco/BR1). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 minutes or until cells sloughed off when flask was banged against hand.

The cells were harvested into 200 ml centrifuge tubes and spun at 1000 rpm, 4° C., for 10 min. The supernatant was discarded and the cells were resuspended in 5 mls/monolayer membrane preparation buffer having the composition: 10 mM Tris pH 7.2–7.4; 4 ug/ml Leupeptin (Sigma); 10 uM Phosphoramidon (Boehringer Mannheim); 40 ug/ml Bacitracin (Sigma); 5 ug/ml Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 minutes.

The pellets were resuspended in 0.2 mls/monolayer membrane prep buffer and aliquots were placed in tubes (500–1000 ul/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM CaCl2; 1 mM MgCl2; 5 mM KCl; 0.2% BSA; 4 ug/ml Leupeptin (SIGMA); 10 uM Phosphoramidon (Boehringer Mannheim); 40 ug/ml Bacitracin (SIGMA); 5 ug/ml Aprotinin (SIGMA); and 10 mM Pefabloc (Boehringer Mannheim). One hundred μl of membrane binding buffer containing 10–40 ug membrane protein was added, followed by 100 μM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 ml per well) with room temperature of filter wash having the composition: 50 mM Tris-HCl pH 7.2 and 20 mM NaCl. The filter was dried, and the bottom sealed and 50 ul of Packard Microscint-20 was added to each well. The top was sealed and the radioactivity quantitated in a Packard Topcount Microplate Scintillation counter.

B. Functional assay. Functional cell based assays were developed to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 March; 11(3): 274–80) were dissociated from tissue culture flasks by rinsing with Ca and Mg free phosphate buffered saline (14190-136, Life Technologies, Gaithersburg, Md.) and detached following 5 minutes incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5 \times 10^6$/ml. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min., cells were lysed by incubation at 100° C. for 5 min. to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min., and an EC50 dose (approximately 10 nM alpha-MSH) was added to the cells. The assay was terminated at 45 min. and cAMP quantitated as above. Percent inhibition was determined by comparing the amount of cAMP produced in the presence to that produced in the absence of test compound.

C. In Vivo Food Intake Models

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276–R1285, 1991; McKenna K E et al, *Modulation By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

Representative compounds of the present invention were tested and found to bind to the melanocortin-4 receptor. These compounds were generally found to have $IC_{50}$ values less than 2 µM. Representative compounds of the present invention were also tested in the functional assay and found generally to activate the melanocortin-4 receptor with $EC_{50}$ values less than 1 µM.

EXAMPLES OF A PHARMACEUTICAL COMPOSITION

As a specific embodiment of an oral composition of a composition of the present invention, 5 mg of Example 2 is formulated with sufficient finely divided lactose to provide a total amount of 580 to 590 mg to fill a size O hard gelatin capsule.

As another specific embodiment of an oral composition of a compound of the present invention, 2.5 mg of Example 2 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

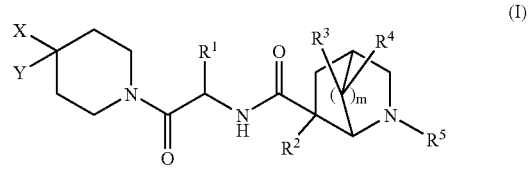

or a pharmaceutically acceptable salt thereof;
wherein m is 1 or 2;
each n is independently 0, 1, or 2;
each p is independently 0, 1 or 2;
q is 1 or 2;
$R^1$ is selected from the group consisting of
  hydrogen,
  $C_{1-8}$ alkyl,
  $(CHR^7)_n$—$C_{3-6}$ cycloalkyl,
  $(CHR^7)_q$—O(CHR$^7$)aryl, (CHR⁷)ₙ-aryl, and
(CHR⁷)ₙ-heteroaryl;
wherein aryl and heteroaryl are unsubstituted or substituted with one to three groups independently selected from R⁶; and alkyl and cycloalkyl are unsubstituted or substituted with one to three groups independently selected from R⁶ and oxo;

R² is selected from the group consisting of
hydrogen,
$C_{1-8}$ alkyl,
$(CH_2)_nC_{3-6}$ cycloalkyl, and
$(CH_2)_n$-aryl;

R³ and R⁴ are each independently selected from the group consisting of
hydrogen,
$C_{1-8}$ alkyl,
$(CH_2)_nC_{3-6}$ cycloalkyl,
$(CH_2)_n$-aryl,
hydroxy,
halogen, and
amino;

R⁵ is selected from the group consisting of
hydrogen,
$C_{1-8}$ alkyl,
$(CH_2)_n$-aryl,
$(CH_2)_nC_{3-6}$ cycloalkyl,
$(CH_2)_n$-heteroaryl,
$(CH_2)_n$-heterocyclyl,
$COC(R^7)_2NH_2$,
$COR^7$,
$(CH_2)_nOR^7$,
$(CH_2)_nCO_2R^7$,
$(CH_2)_nCONR^7R^7$,
$CH_2C\equiv CH$,
$CO_2R^7$,
$CH_2CHF_2$,
$CONR^7R^7$, and
$SO_2R^7$;
wherein aryl and heteroaryl are unsubstituted or substituted with one to three groups independently selected from R⁶; and alkyl, cycloalkyl, and heterocyclyl are unsubstituted or substituted with one to three groups independently selected from R⁶ and oxo;

each R⁶ is independently selected from the group consisting of
hydrogen,
$C_{1-6}$ alkyl,
$(CH_2)_n$-phenyl,
$(CH_2)_n$-naphthyl,
$(CH_2)_n$-heteroaryl,
$(CH_2)_n$-heterocyclyl,
$(CH_2)_nC_{3-7}$ cycloalkyl,
halogen,
$OR^7$,
$(CH_2)_nN(R^7)_2$,
$(CH_2)_nC\equiv N$,
$(CH_2)_nCO_2R^7$,
$NO_2$,
$(CH_2)_nNR^7SO_2R^7$,
$(CH_2)_nSO_2N(R^7)_2$,
$(CH_2)_nS(O)_pR^7$,
$(CH_2)_nNR^7C(O)N(R^7)_2$,
$(CH_2)_nC(O)N(R^7)_2$,
$(CH_2)_nNR^7C(O)R^7$,
$(CH_2)_nNR^7CO_2R^7$,
$O(CH_2)_nC(O)N(R^7)_2$,
$CF_3$,
$CH_2CF_3$,
$OCF_3$, and
$OCH_2CF_3$;
wherein phenyl, naphthyl, heteroaryl, cycloalkyl, and heterocyclyl are unsubstituted or substituted with one to three substituents independently selected from halogen, hydroxy, $C_{1-4}$ alkyl, trifluoromethyl, and $C_{1-4}$ alkoxy; and wherein any methylene ($CH_2$) carbon atom in R⁶ is unsubstituted or substituted with one to two groups independently selected from halogen, hydroxy, and $C_{1-4}$ alkyl; or two substituents when on the same methylene ($CH_2$) carbon atom are taken together with the carbon atom to which they are attached to form a cyclopropyl group;

each R⁷ is independently selected from the group consisting of
hydrogen,
$C_{1-8}$ alkyl,
$(CH_2)_n$-phenyl,
$(CH_2)_n$-naphthyl,
$(CH_2)_n$-heteroaryl, and
$(CH_2)_nC_{3-7}$ cycloalkyl;
wherein phenyl, naphthyl, and heteroaryl are unsubstituted or substituted with one to three groups independently selected from R⁶; alkyl and cycloalkyl are unsubstituted or substituted with one to three groups independently selected from R⁶ and oxo; and wherein any methylene ($CH_2$) carbon atom in R⁷ is unsubstituted or substituted with one to two groups independently selected from halogen, hydroxy, and $C_{1-4}$ alkyl; or two R⁷ groups together with the atom to which they are attached form a 5- to 8-membered mono- or bicyclic ring system optionally containing an additional heteroatom selected from O, S, and $NC_{1-4}$ alkyl;

each R⁸ is independently selected from the group consisting of
hydrogen,
$(CH_2)_nC_{1-7}$ alkyl,
$(CH_2)_n$-aryl,
$(CH_2)_n$-heteroaryl,
$(CH_2)_n$-heterocyclyl, and
$(CH_2)_nC_{3-7}$ cycloalkyl;
wherein aryl and heteroaryl are unsubstituted or substituted with one to three groups independently selected from R⁶; and alkyl, cycloalkyl, heterocyclyl, and $(CH_2)_n$ are unsubstituted or substituted with one to three groups independently selected from R⁶ and oxo; or two substituents when on the same methylene ($CH_2$) carbon atom are taken together with the carbon atom to which they are attached to form a cyclopropyl group;
or two R⁸ groups together with the atoms to which they are attached form a 5- to 8-membered mono- or bicyclic ring system optionally containing an additional heteroatom selected from O, S, NR⁷, NBoc, and NCbz;

X is selected from the group consisting of
$C_{1-8}$ alkyl,
$(CH_2)_nC_{3-8}$ cycloalkyl,
$(CH_2)_n$-phenyl,
$(CH_2)_n$-naphthyl,
$(CH_2)_n$-heteroaryl,
$(CH_2)_n$heterocyclyl,
$(CH_2)_nC\equiv N$,
$(CH_2)_nCON(R^8R^8)$,
$(CH_2)_nCO_2R^8$,
$(CH_2)_nCOR^8$,
$(CH_2)_nNR^8C(O)R^8$,
$(CH_2)_nNR^8CO_2R^8$, $(CH_2)_nNR^8C(O)N(R^8)_2$,
$(CH_2)_nNR^8SO_2R^8$,
$(CH_2)_nS(O)_pR^8$,
$(CH_2)_nSO_2N(R^8)(R^8)$,
$(CH_2)_nOR^8$,
$(CH_2)_nOC(O)R^8$,
$(CH_2)_nOC(O)OR^8$,
$(CH_2)_nOC(O)N(R^8)_2$,
$(CH_2)_nN(R^8)(R^8)$, and
$(CH_2)_nNR^8SO_2N(R^8)(R^8)$;

wherein phenyl, naphthyl, and heteroaryl are unsubstituted or substituted with one to three groups independently selected from $R^6$; alkyl, cycloalkyl, and heterocyclyl are unsubstituted or substituted with one to three groups independently selected from $R^6$ and oxo; and wherein any methylene ($CH_2$) carbon atom in X is unsubstituted or substituted with one to two groups independently selected from halogen, hydroxy, and $C_{1-4}$ alkyl; and Y is selected from the group consisting of
hydrogen,
$C_{1-8}$ alkyl,
$C_{2-6}$ alkenyl,
$(CH_2)_nC_{3-8}$ cycloalkyl,
$(CH_2)_n$-phenyl,
$(CH_2)_n$-naphthyl,
$(CH_2)_n$-heteroaryl, and
$(CH_2)_n$-heterocyclyl;

wherein phenyl, naphthyl, and heteroaryl are unsubstituted or substituted with one to three groups independently selected from $R^6$; alkyl, cycloalkyl, and heterocyclyl are optionally substituted with one to three groups independently selected from $R^6$ and oxo; and wherein any methylene ($CH_2$) carbon atom in Y is unsubstituted or substituted with one to two groups independently selected from halogen, hydroxy, and $C_{1-4}$ alkyl.

2. The compound of claim 1 wherein $R^1$ is $CHR^7$-aryl, $CHR^7OCHR^7$-aryl, or $CHR^7$-heteroaryl wherein aryl and heteroaryl are unsubstituted or substituted with one to two groups independently selected from $R^6$.

3. The compound of claim 2 wherein $R^1$ is benzyl optionally substituted with one or two groups independently selected from halogen, $C_{1-4}$ alkyl, $C_{1-4}$ alkoxy, CN, $CF_3$, and $OCF_3$.

4. The compound of claim 3 wherein $R^1$ is 4-chlorobenzyl; 4-fluorobenzyl; 3,4-difluorobenzyl; 3,5-difluorobenzyl; 2-cyano-4-fluorobenzyl; or 4-methoxybenzyl.

5. The compound of claim 1 wherein $R^2$ is hydrogen or methyl.

6. The compound of claim 1 wherein $R^5$ is selected from the group consisting of
hydrogen,
$C_{1-8}$ alkyl,
$(CH_2)_n$-aryl,
$(CH_2)_n$-heteroaryl,
$(CH_2)_n$-heterocyclyl,
$(CH_2)_nC_{3-6}$ cycloalkyl,
$(CH_2)_nCO_2R^7$,
$(CH_2)_nCONR^7R^7$,
$(CH_2)_nOR^7$,
$COC(R^7)NH_2$,
$CH_2C\equiv CH$, and
$CH_2CHF_2$;

wherein aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo.

7. The compound of claim 6 wherein X is selected from the group consisting of
$C_{1-6}$ alkyl,
$(CH_2)_n$-aryl,
$(CH_2)_n$-heteroaryl,
$(CH_2)_n$-heterocyclyl,
$(CH_2)_nC(O)N(R^8)(R^8)$,
$(CH_2)_nCO_2R^8$,
$(CH_2)_nOR^8$,
$(CH_2)_nS(O)_{0-2}R^8$,
$(CH_2)_nNHC(O)R^8$,
$(CH_2)_nOC(O)NR^8R^8$, and
$(CH_2)_nNR^8SO_2R^8$;

wherein aryl and heteroaryl are optionally substituted with one to three groups independently selected from $R^6$; heterocyclyl is optionally substituted with one to three groups independently selected from $R^6$ and oxo; the $(CH_2)_n$ group is optionally substituted with one to three groups independently selected from $R^7$, halogen, $S(O)_{0-2}R^7$, $N(R^7)_2$, and $OR^7$; and each $R^8$ is independently selected from H, $C_{1-8}$ alkyl, and $C_{3-6}$ cycloalkyl, wherein alkyl and cycloalkyl are optionally substituted with one to three groups independently selected from $R^6$ and oxo; or two $R^8$ groups together with the atoms to which they are attached form a 5- to 8-membered mono- or bi-cyclic ring system optionally containing an additional heteroatom selected from O, S, $NR^7$, NBoc, and NCbz.

8. The compound of claim 7 wherein X is selected from the group consisting of
$C_{1-6}$ alkyl,
$(CH_2)_{0-1}$-heteroaryl,
$CH_2$-heterocyclyl,
$CO_2R^8$,
$CH_2OR^8$,
$CH_2S(O)_{0-2}R^8$,
$NHC(O)R^8$,
$CH_2NR^8SO_2R^8$,
$CH_2OC(O)NR^8R^8$,
$CH_2NR^8SO_2R^8$, and
$C(O)N(R^8)(R^8)$;

wherein heteroaryl is optionally substituted with one to three groups independently selected from $R^6$; heterocyclyl is optionally substituted with one to three groups independently selected from $R^6$ and oxo; and each $R^8$ is independently selected from H, $C_{1-8}$ alkyl, and $C_{3-6}$ cycloalkyl, wherein alkyl and cycloalkyl are optionally substituted with one to three groups independently selected from $R^6$ and oxo; or two $R^8$ groups together with the atoms to which they are attached form a 5- to 8-membered mono- or bi-cyclic ring system optionally containing an additional heteroatom selected from O, S, $NR^7$, NBoc, and NCbz.

9. The compound of claim 1 wherein Y is selected from the group consisting of
$C_{1-8}$ alkyl,
$(CH_2)_nC_{3-7}$ cycloalkyl,
$(CH_2)_n$-aryl,
$(CH_2)_n$-heterocyclyl, and
$(CH_2)_n$-heteroaryl;

wherein aryl and heteroaryl are optionally substituted with one to three groups independently selected from $R^6$; and $(CH_2)_n$, alkyl, cycloalkyl, and heterocyclyl are optionally substituted with one to three groups independently selected from $R^6$ and oxo.

10. The compound of claim 9 wherein Y is
cyclohexyl,
cycloheptyl,
cyclopentyl, or
$C_{1-6}$ alkyl;
wherein alkyl and cycloalkyl groups are unsubstituted or substituted with one to three groups independently selected from $R^6$ and oxo.

11. The compound of claim 10 wherein Y is cyclohexyl or $C_{1-6}$ alkyl; wherein the cyclohexyl and alkyl groups are unsubstituted or substituted with one to three groups independently selected from $R^6$ and oxo.

12. The compound of claim 1 of formula II:

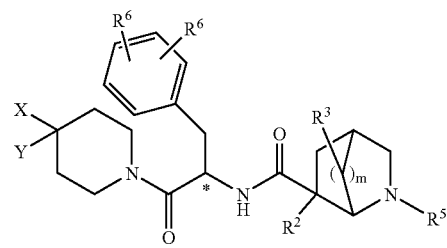

(II)

wherein m is 1 or 2;
each n is independently 0, 1, or 2;
$R^2$ is hydrogen or methyl;
$R^3$ is hydrogen, fluoro, or hydroxy;
each $R^6$ is independently selected from the group consisting of
  hydrogen,
  halogen,
  cyano,
  $C_{1-4}$ alkyl,
  $C_{1-4}$ alkoxy,
  trifluoromethyl, and
  trifluoromethoxy;
$R^5$ is selected from the group consisting of
  hydrogen,
  $C_{1-8}$ alkyl,
  $(CH_2)_n$-aryl,
  $(CH_2)_n$-heteroaryl,
  $(CH_2)_n$-heterocyclyl,
  $(CH_2)_n C_{3-6}$ cycloalkyl,
  $(CH_2)_n CO_2 R^7$,
  $(CH_2)_n CONR^7 R^7$,
  $(CH_2)_n OR^7$,
  $COC(R^7)NH_2$,
  $CH_2 C\equiv CH$, and
  $CH_2 CHF_2$;
wherein aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;
Y is selected from the group consisting of
  $C_{5-7}$ cycloalkyl and
  $C_{1-6}$ alkyl;
wherein alkyl and cycloalkyl are unsubstituted or substituted with one to three groups independently selected from $R^6$ and oxo; and X is selected from the group consisting of

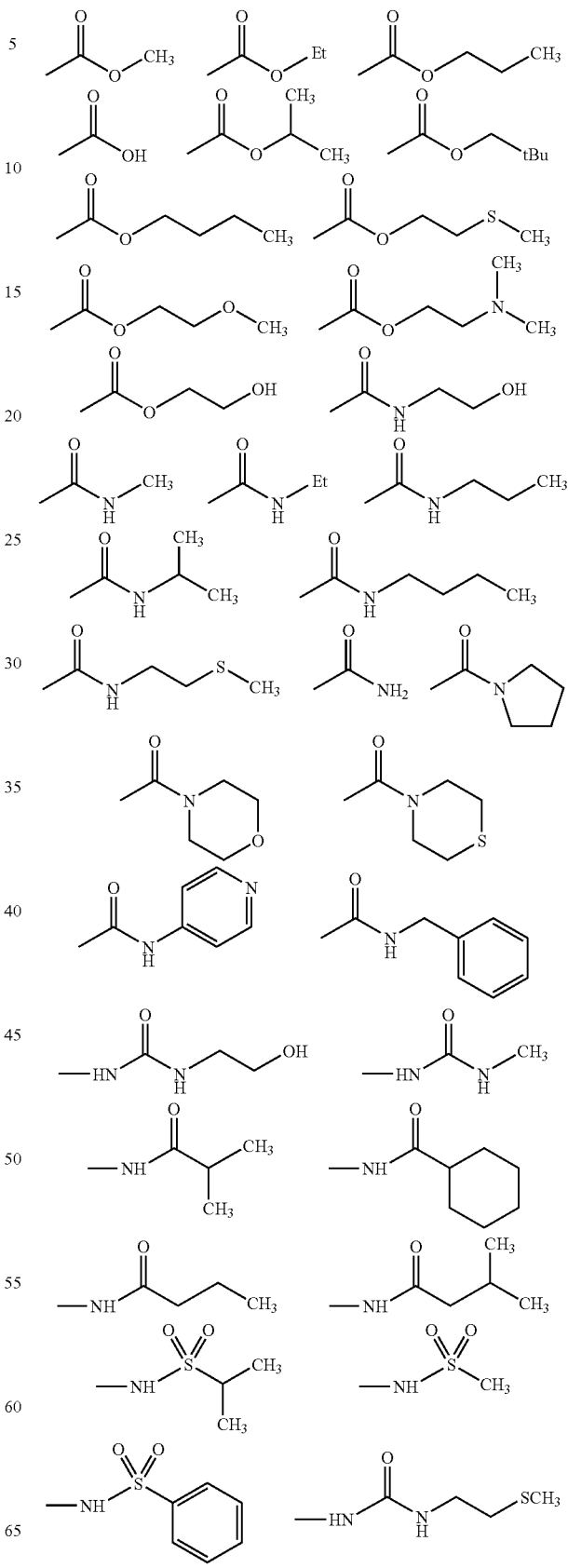

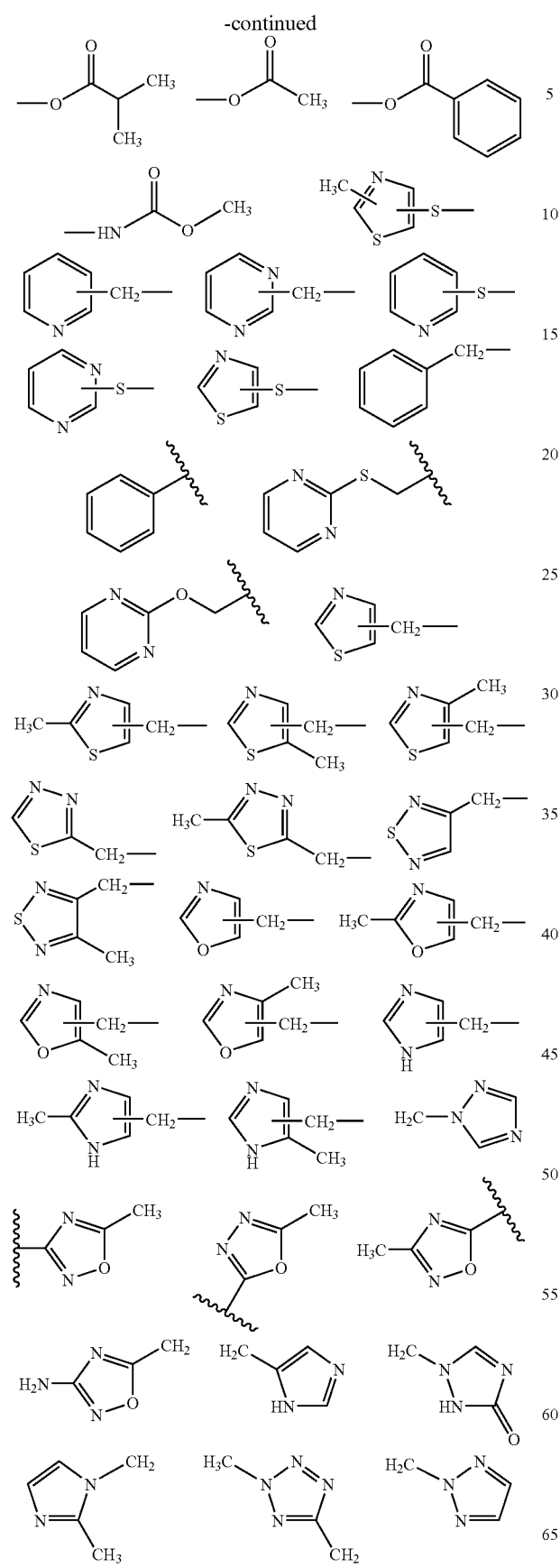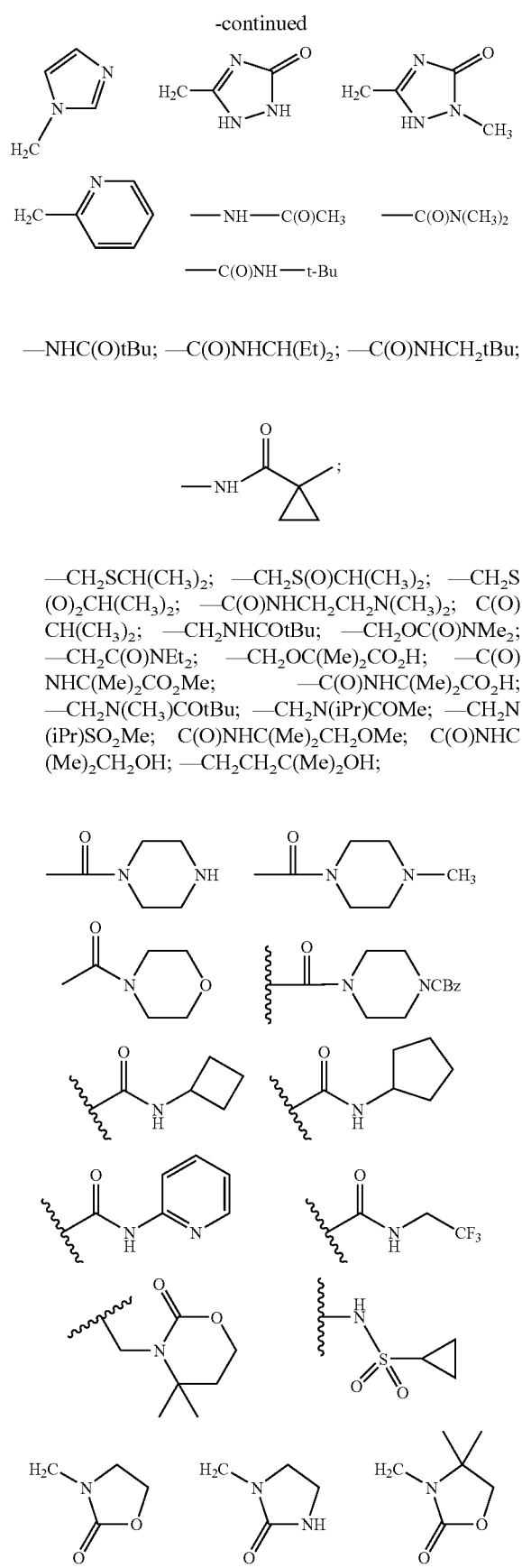

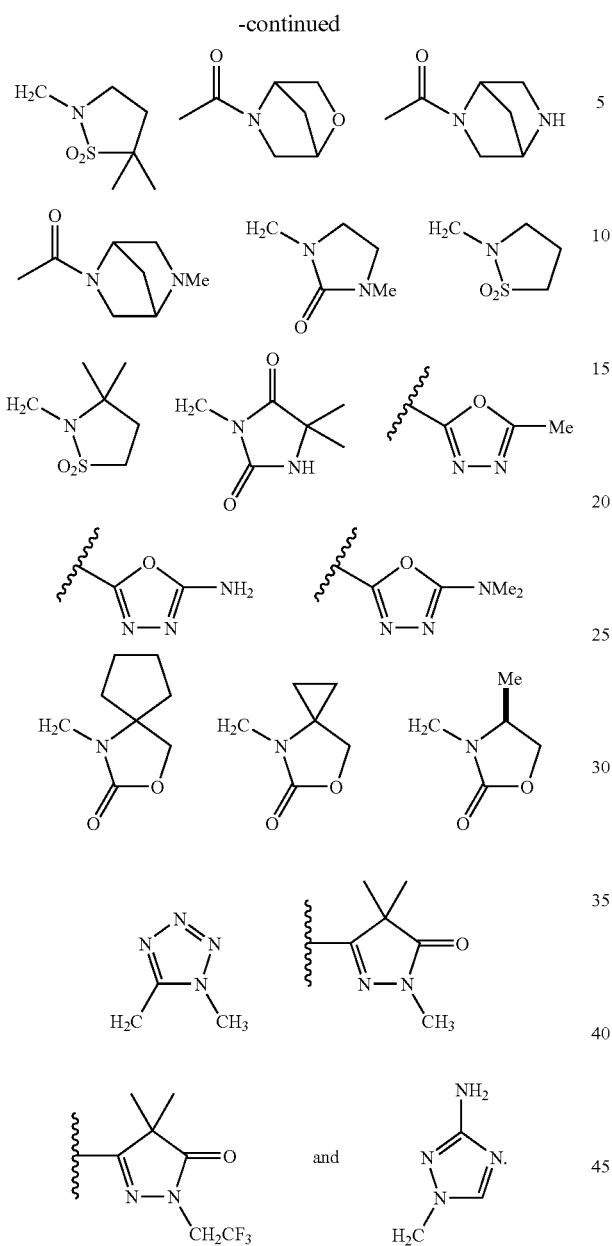
13. The compound of claim 12 wherein the carbon atom marked with an * has the R configuration.
14. The compound of claim 13 selected from the group consisting of:
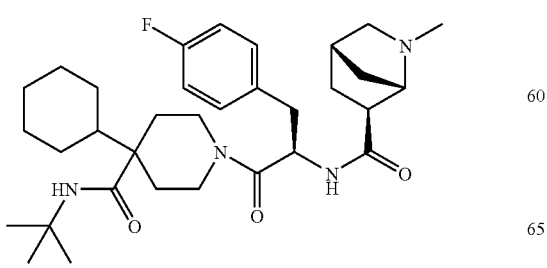
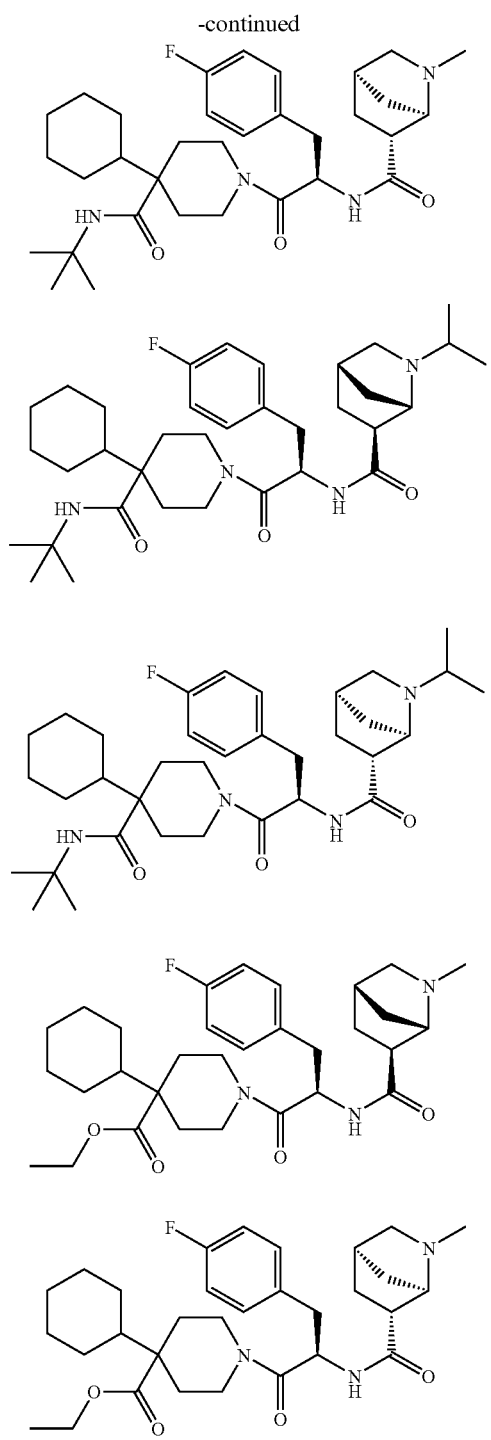
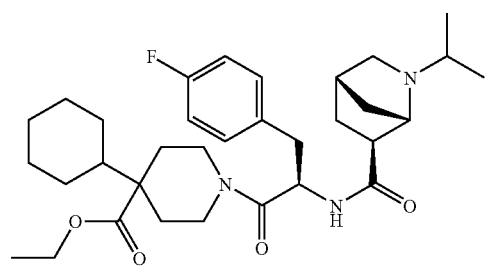

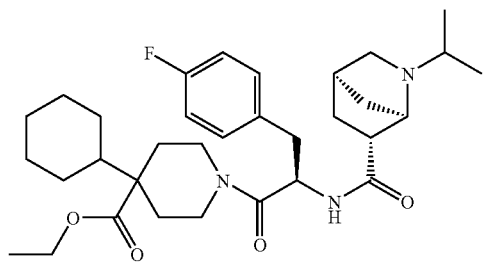
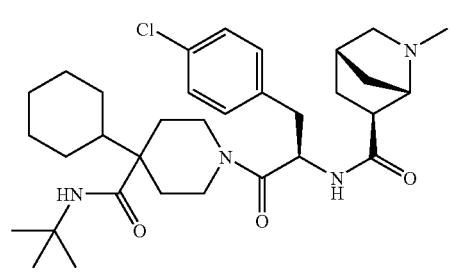
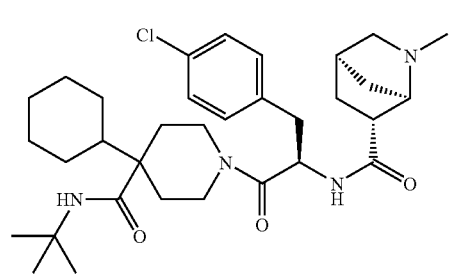
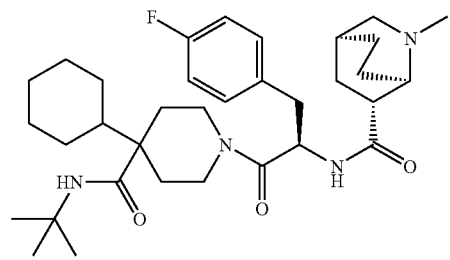
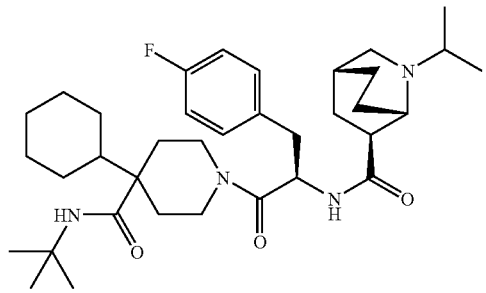
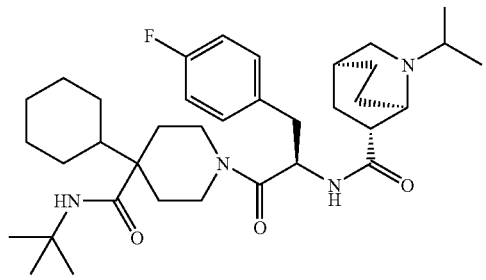
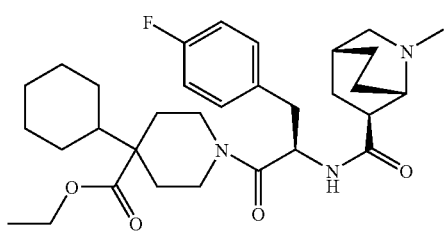
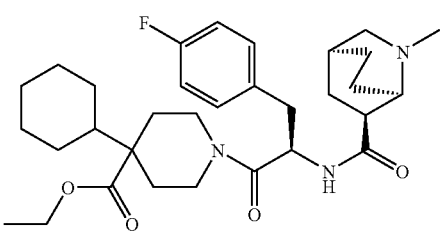
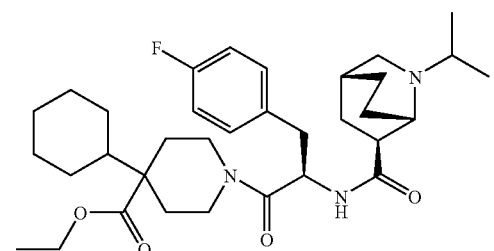
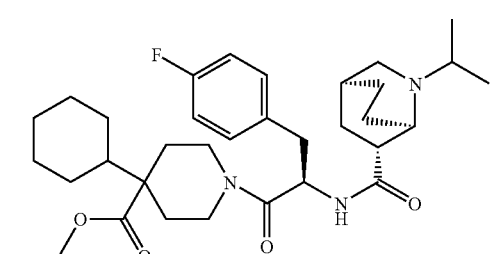
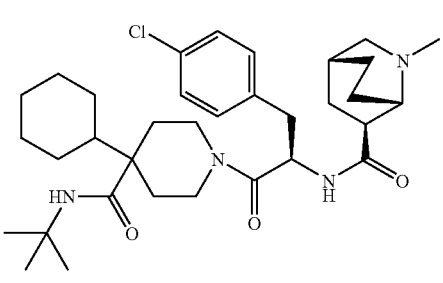
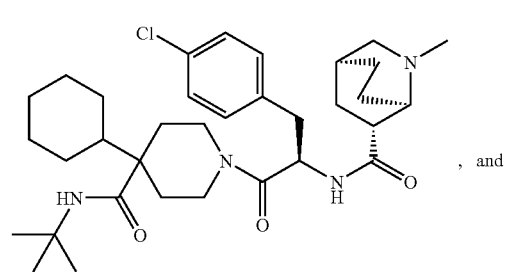, and -continued

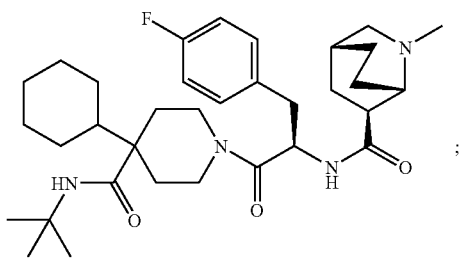

or a pharmaceutically acceptable salt thereof.

15. A pharmaceutical composition which comprises a therapeutically effective amount of a compound of claim 1 and a pharmaceutically acceptable carrier.

16. A method for the treatment of obesity in a subject in need thereof which comprises administering to the subject a therapeutically effective amount of a compound according to claim 1.

17. A method for the treatment of diabetes mellitus in a subject in need thereof comprising administering to the subject a therapeutically effective amount of a compound according to claim 1.

18. A method for the treatment of male or female sexual dysfunction in a subject in need thereof comprising administering to the subject a therapeutically effective amount of a compound according to claim 1.

19. A method for the treatment of erectile dysfunction in a subject in need thereof comprising administering to the subject a therapeutically effective amount of a compound according to claim 1.

* * * * *